US011649458B2

(12) United States Patent
Daugherty et al.

(10) Patent No.: US 11,649,458 B2
(45) Date of Patent: May 16, 2023

(54) INHIBITING ANGIOTENSINOGEN TO ATTENUATE AORTIC PATHOLOGY IN MARFAN SYNDROME

(71) Applicant: UNIVERSITY OF KENTUCKY RESEARCH FOUNDATION, Lexington, KY (US)

(72) Inventors: Alan Daugherty, Lexington, KY (US); Hong Lu, Lexington, KY (US); Mary Sheppard, Lexington, KY (US); Jeff Chen, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 72 days.

(21) Appl. No.: 17/308,895

(22) Filed: May 5, 2021

(65) Prior Publication Data
US 2021/0348168 A1    Nov. 11, 2021

Related U.S. Application Data

(60) Provisional application No. 63/020,324, filed on May 5, 2020.

(51) Int. Cl.
| | |
|---|---|
| C07H 21/04 | (2006.01) |
| C12N 15/113 | (2010.01) |
| A61K 31/7088 | (2006.01) |
| A61P 9/10 | (2006.01) |
| A61K 31/4178 | (2006.01) |

(52) U.S. Cl.
CPC ...... *C12N 15/1136* (2013.01); *A61K 31/4178* (2013.01); *A61K 31/7088* (2013.01); *A61P 9/10* (2018.01); *C12N 2310/11* (2013.01); *C12N 2310/351* (2013.01)

(58) Field of Classification Search
None
See application file for complete search history.

(56) References Cited

U.S. PATENT DOCUMENTS

| | | |
|---|---|---|
| 10,709,728 B2 | 7/2020 | Hinkle |
| 10,912,792 B2 | 2/2021 | Mullick et al. |
| 2015/0297629 A1 | 10/2015 | Mullick et al. |
| 2019/0160090 A1* | 5/2019 | Mullick ............... C12N 15/113 |

OTHER PUBLICATIONS

Yu, Christopher, and Richmond W. Jeremy. "Angiotensin, transforming growth factor β and aortic dilatation in Marfan syndrome: of mice and humans." IJC Heart & Vasculature 18 (2018): 71-80.*
Salameh, Maya J., James H. Black III, and Elizabeth V. Ratchford. "Thoracic aortic aneurysm." Vascular Medicine 23.6 (2018): 573-578.*

Al-Abcha A, Saleh Y, Mujer M, et al. Meta-analysis examining the usefulness of angiotensin receptor blockers for the prevention of aortic root dilation in patients with the Marfan syndrome. Am J Cardiol 2020;128:101-106.
Bhatt AB, Buck JS, Zuflacht JP, Milian J, Kadivar S, Gauvreau K, Singh MN, Creager MA. Distinct Effects of Losartan and Atenolol on Vascular Stiffness in Marfan Syndrome. Vascular medicine (London, England). 2015;20(4):317-25. Epub Mar. 22, 2015. doi: 10.1177/1358863x15569868. PubMed PMID: 25795452.
Brooke BS, Habashi JP, Judge DP, Patel N, Loeys B, Dietz HC, 3rd. Angiotensin Ii Blockade and Aortic-Root Dilation in Marfan's Syndrome. N Engl J Med. 2008;358(26):2787-95. doi: 10.1056/NEJMoa0706585. PubMed PMID: 18579813; PMCID: PMC2692965.
Chen JZ, Sawada H, Moorleghen JJ, Weiland M, Daugherty A, Sheppard MB. Aortic Strain Correlates with Elastin Fragmentation in Fibrillin-1 Hypomorphic Mice. Circ Rep. 2019;1(5):199-205. doi: 10.1253/circrep.CR-18-0012. PubMed PMID: 31123721; PMCID: PMC6528667.
Chen, J.Z., et al. (2020), "Inhibition of Angiotensin II Dependent AT1a Receptor Stimulation Attenuates Thoracic Aortic Pathology in Fibrillin-1C1041G/+ Mice," bioRxiv preprint, Jun. 2, 2020, doi: doi.org/10.1101/2020.06.01.127670.
Chen, JZ (2020) "Involvement of the Renin Angiotensin System in Marfan Syndrome Associated Thoracic Aortic Aneurysms," Theses and Dissertations—Physiology. 47. uknowledge.uky.edu/physiology_etds/47.
Cook JR, Carta L, Benard L, Chemaly ER, Chiu E, Rao SK, Hampton TG, Yurchenco P, Gen TACRC, Costa KD, Hajjar RJ, Ramirez F. Abnormal Muscle Mechanosignaling Triggers Cardiomyopathy in Mice with Marfan Syndrome. The Journal of clinical investigation. 2014;124(3):1329-39.
Cook JR, Clayton NP, Carta L, Galatioto J, Chiu E, Smaldone S, Nelson CA, Cheng SH, Wentworth BM, Ramirez F. Dimorphic Effects of Transforming Growth Factor-Beta Signaling During Aortic Aneurysm Progression in Mice Suggest a Combinatorial Therapy for Marfan Syndrome. Arterioscler Thromb Vasc Biol. 2015;35(4):911-7.
Daugherty A, Tall AR, Daemen M, Falk E, Fisher EA, Garcia-Cardena G, Lusis AJ, Owens AP, 3rd, Rosenfeld ME, Virmani R. Recommendation on Design, Execution, and Reporting of Animal Atherosclerosis Studies: A Scientific Statement from the American Heart Association. Arterioscler Thromb Vasc Biol. 2017;37(9):e131-e57.
Dietz HC, Cutting CR, Pyeritz RE, Maslen CL, Sakai LY, Corson GM, Puffenberger EG, Hamosh A, Nanthakumar EJ, Curristin SM, Stetten G, Meyers DA, Francomano CA. Marfan Syndrome Caused by a Recurrent De Novo Missense Mutation in the Fibrillin Gene. Nature. 1991;352(6333):337-9. Epub Jul. 25, 1991. doi: 10.1038/352337a0. PubMed PMID:1852208.
Ding Y, Stec DE, Sigmund CD. Genetic Evidence That Lethality in Angiotensinogen-Deficient Mice is Due to Loss of Systemic but Not Renal Angiotensinogen. J Biol Chem. 2001;276(10):7431-6. Epub Nov. 30, 2000. doi: 10.1074/jbc.M003892200. PubMed PMID: 11096065.

(Continued)

*Primary Examiner* — Kimberly Chong
(74) *Attorney, Agent, or Firm* — Stites & Harbison PLLC; Mandy Wilson Decker

(57) ABSTRACT

Disclosed herein is a method for attenuating aortic pathology in a subject having Marfan syndrome by reducing angiotensinogen plasma levels in the subject.

20 Claims, 23 Drawing Sheets

Specification includes a Sequence Listing.

(56) References Cited

OTHER PUBLICATIONS

Galatioto J, Caescu CI, Hansen J, Cook JR, Miramontes I, Iyengar R, Ramirez F. Cell Type-Specific Contributions of the Angiotensin Ii Type 1a Receptor to Aorta Homeostasis and Aneurysmal Disease-Brief Report. Arterioscler Thromb Vasc Biol. 2018;38(3):588-91. Epub Jan. 27, 2018. doi: 10.1161/ATVBAHA.117.310609. PubMed PMID: 29371244; PMCID: PMC5823778.

Gallo EM, Loch DC, Habashi JP, Calderon JF, Chen Y, Bedja D, van Erp C, Gerber EE, Parker SJ, Sauls K, Judge DP, Cooke SK, Lindsay ME, Rouf R, Myers L, ap Rhys CM, Kent KC, Norris RA, Huso DL, Dietz HC. Angiotensin Ii-Dependent Tgf-Beta Signaling Contributes to Loeys-Dietz Syndrome Vascular Pathogenesis. The Journal of clinical investigation. 2014;124(1):448-60. doi: 10.1172/JCI69666. PubMed PMID: 24355923; PMCID: PMC3871227.

Habashi JP, Doyle JJ, Holm TM, Aziz H, Schoenhoff F, Bedja D, Chen Y, Modiri AN, Judge DP, Dietz HC. Angiotensin Ii Type 2 Receptor Signaling Attenuates Aortic Aneurysm in Mice through Erk Antagonism. Science. 2011;332(6027):361-5. doi: 10.1126/science.1192152. PubMed PMID: 21493863; PMCID: PMC3097422.

Habashi JP, Judge DP, Holm TM, Cohn RD, Loeys BL, Cooper TK, Myers L, Klein EC, Liu G, Calvi C, Podowski M, Neptune ER, Halushka MK, Bedja D, Gabrielson K, Rifkin DB, Carta L, Ramirez F, Huso DL, Dietz HC. Losartan, an At1 Antagonist, Prevents Aortic Aneurysm in a Mouse Model of Marfan Syndrome. Science. 2006;312(5770):117-21. doi: 10.1126/science.1124287. PubMed PMID: 16601194; PMCID: PMC1482474.

Hibender S, Franken R, van Roomen C, Ter Braake A, van der Made I, Schermer EE, Gunst Q, van den Hoff MJ, Lutgens E, Pinto YM, Groenink M, Zwinderman AH, Mulder BJ, de Vries CJ, de Waard V. Resveratrol Inhibits Aortic Root Dilatation in the Fbn1c1039g/+ Marfan Mouse Model. Arterioscler Thromb Vasc Biol. 2016;36(8):1618-26. doi: 10.1161/ATVBAHA.116.307841. PubMed PMID: 27283746.

Ito M, Oliverio MI, Mannon PJ, Best CF, Maeda N, Smithies O, Coffman TM. Regulation of Blood Pressure by the Type 1a Angiotensin Ii Receptor Gene. Proc Natl Acad Sci U S A. 1995;92(8):3521-5. PubMed PMID: 7724593; PMCID: PMC42199.

Iwasaki H, Yoshimoto T, Sugiyama T, Hirata Y. Activation of Cell Adhesion Kinase Beta by Mechanical Stretch in Vascular Smooth Muscle Cells. Endocrinology. 2003;144(6):2304-10. Epub May 15, 2003. doi: 10.1210/en.2002-220939. PubMed PMID: 12746290.

Judge DP, Biery NJ, Keene DR, Geubtner J, Myers L, Huso DL, Sakai LY, Dietz HC. Evidence for a Critical Contribution of Haploinsufficiency in the Complex Pathogenesis of Marfan Syndrome. The Journal of clinical investigation. 2004;114(2):172-81. doi: 10.1172/JCI20641. PubMed PMID: 15254584; PMCID: PMC449744.

Kuang SQ, Geng L, Prakash SK, Cao JM, Guo S, Villamizar C, Kwartler CS, Peters AM, Brasier AR, Milewicz DM. Aortic Remodeling after Transverse Aortic Constriction in Mice is Attenuated with At1 Receptor Blockade. Arterioscler Thromb Vasc Biol. 2013;33(9):2172-9. doi: 10.1161/ATVBAHA.113.301624. PubMed PMID: 23868934.

Lacro RV, Dietz HC, Sleeper LA, et al. Atenolol versus losartan in children and young adults with Marfan's syndrome. N. Engl. J. Med. 2014;371:2061-2071.

Lee B, Godfrey M, Vitale E, Hori H, Mattei MG, Sarfarazi M, Tsipouras P, Ramirez F, Hollister DW. Linkage of Marfan Syndrome and a Phenotypically Related Disorder to Two Different Fibrillin Genes. Nature. 1991;352(6333):330-4. Epub Jul. 25, 1991. doi: 10.1038/352330a0. PubMed PMID: 1852206.

Lu H, Wu C, Howatt DA, Balakrishnan A, Moodeghen JJ, Chen X, Zhao M, Graham MJ, Mullick AE, Crooke RM, Feldman DL, Cassis LA, Vander Kooi CW, Daugherty A. Angiotensinogen Exerts Effects Independent of Angiotensin Ii. Arterioscler Thromb Vasc Biol. 2016;36(2):256-65. doi: 10.1161/ATVBAHA.115.306740. PubMed PMID: 26681751; PMCID: PMC4732917.

Mangrum AJ, Gomez RA, Norwood VF. Effects of at(1a) Receptor Deletion on Blood Pressure and Sodium Excretion During Altered Dietary Salt Intake. American journal of physiology Renal physiology. 2002;283(3):F447-53. Epub Aug. 9, 2002. doi: 10.1152/ajprenal.00259.2001. PubMed PMID: 12167595.

Milewicz DM, Ramirez F. Therapies for thoracic aortic aneurysms and acute aortic dissections. Arterioscler Thromb Vasc Biol 2019;39:126-136.

Mullen M, Jin XY, Child A, Stuart AG, Dodd M, Aragon-Martin JA, Gaze D, Kiotsekoglou A, Yuan L, Hu J, Foley C, Van Dyck L, Knight R, Clayton T, Swan L, Thomson JDR, Erdem G, Crossman D, Flather M, Investigators A. Irbesartan in Marfan Syndrome (Aims): A Double-Blind, Placebo-Controlled Randomised Trial. Lancet. 2020;394(10216):2263-70. Epub Dec. 15, 2019. doi: 10.1016/S0140-6736(19)32518-8. PubMed PMID: 31836196; PMCID: PMC6934233.

Poduri A, Owens AP, 3rd, Howatt DA, Moodeghen JJ, Balakrishnan A, Cassis LA, Daugherty A. Regional Variation in Aortic At1b Receptor Mrna Abundance is Associated with Contractility but Unrelated to Atherosclerosis and Aortic Aneurysms. PloS one. 2012;7(10):e48462. Epub Nov. 3, 2012 doi: 10.1371/journal.pone.0048462. PubMed PMID: 23119030; PMCID: PMC3485205.

Ramnath NW, Hawinkels LJ, van Heijningen PM, te Riet L, Paauwe M, Vermeij M, Danser AH, Kanaar R, ten Dijke P, Essers J. Fibulin-4 Deficiency Increases Tgf-Beta Signalling in Aortic Smooth Muscle Cells Due to Elevated Tgf-Beta2 Levels. Sci Rep. 2015;5:16872. doi: 10.1038/srep16872. PubMed PMID: 26607280; PMCID: PMC4660353.

Rateri DL, Davis FM, Balakrishnan A, Howatt DA, Moorleghen JJ, O'Connor WN, Charnigo R, Cassis LA, Daugherty A. Angiotensin Ii Induces Region-Specific Medial Disruption During Evolution of Ascending Aortic Aneurysms. Am J Pathol. 2014;184(9):2586-95. doi: 10.1016/j.ajpath.2014.05.014. PubMed PMID: 25038458; PMCID: 25038458.

Renard M, Muino-Mosquera L, Manalo EC, Tufa S, Carlson EJ, Keene DR, De Backer J, Sakai LY. Sex, Pregnancy and Aortic Disease in Marfan Syndrome. PloS one. 2017;12(7):e0181166. Epub Jul. 15, 2017. doi: 10.1371/journal.pone.0181166. PubMed PMID: 28708846.

Robinet P, Milewicz DM, Cassis LA, Leeper NJ, Lu HS, Smith JD. Consideration of Sex Differences in Design and Reporting of Experimental Arterial Pathology Studies—Statement from Atvb Council. Arterioscler Thromb Vasc Biol. 2018;38(2):292-303 Epub Jan. 6, 2018. doi: 10.1161/atvbaha.117.309524. PubMed PMID: 29301789; PMCID: PMC5785439.

Sadoshima J. Novel at(1) Receptor-Independent Functions of Losartan. Circ Res. 2002;90(7):754-6. PubMed PMID: 11964366.

Sawada H, Chen JZ, Wright BC, Moorleghen JJ, Lu HS, Daugherty A. Ultrasound Imaging of the Thoracic and Abdominal Aorta in Mice to Determine Aneurysm Dimensions. J Vis Exp. 2019;8(145):10.3791/59013. Epub Mar. 26, 2019. doi: 10.3791/59013. PubMed PMID: 30907888; PMCID: PMC6594159.

Schleifenbaum J, Kassmann M, Szijártó IA, Hercule HC, Tano JY, Weinert S, Heidenreich M, Pathan AR, Anistan YM, Alenina N, Rusch NJ, Bader M, Jentsch TJ, Gollasch M. Stretch-Activation of Angiotensin Ii Type 1a Receptors Contributes to the Myogenic Response of Mouse Mesenteric and Renal Arteries. Circ Res. 2014;115(2):263-72. Epub May 20, 2014. doi: 10.1161/circresaha.115.302882. PubMed PMID: 24838176.

Sellers SL, Milad N, Chan R, Mielnik M, Jermilova U, Huang PL, de Crom R, Hirota JA, Hogg JC, Sandor GG, Van Breemen C, Esfandiarei M, Seidman MA, Bernatchez P. Inhibition of Marfan Syndrome Aortic Root Dilation by Losartan: Role of Angiotensin Ii Receptor Type 1-Independent Activation of Endothelial Function. Am J Pathol. 2018;188(3):574-85. Epub Feb. 13, 2018. doi: 10.1016/j.ajpath.2017.11.006. PubMed PMID: 29433732.

Sheppard MB, Chen JZ, Rateri DL, Moorleghen JJ, Weiland M, and Daugherty A, (2019) Abstract "Renin-Angiotensin System Inhibitors Do Not Improve Survival in Fibrillin-1 Hypomorphic Mice with Established Aortic Aneurysm," J Clin Transl Sci. Mar. 2019; 3(Suppl 1): 112-113.

Smith JD, Chen JZ, Phillips R, Daugherty A, Sheppard MB, (2021) "Losartan Increases Survival of the Fbn1mgR/mgR Mouse Model of Marfan Syndrome in an Age-Dependent Manner," bioRxiv preprint, Feb. 20, 2021, doi: doi.org/10.1101/2021.02.19.429438.

(56) References Cited

OTHER PUBLICATIONS

Wu CH, Wang Y, Ma M, Mullick AE, Crooke RM, Graham MJ, Daugherty A, Lu HS. Antisense Oligonucleotides Targeting Angiotensinogen: Insights from Animal Studies. Bioscience reports. 2019;39(1). Epub Dec. 12, 2018. doi: 10.1042/BSR20180201. PubMed PMID: 30530571; PMCID: PMC6328882.

Yang HH, Kim JM, Chum E, van Breemen C, Chung AW. Long-Term Effects of Losartan on Structure and Function of the Thoracic Aorta in a Mouse Model of Marfan Syndrome. British journal of pharmacology. 2009;158(6):1503-12. doi: 10.1111/j.1476-5381.2009.00443.x. PubMed PMID: 19814725; PMCID: PMC2795217.

Yasuda N, Miura S, Akazawa H, Tanaka T, Qin Y, Kiya Y, Imaizumi S, Fujino M, Ito K, Zou Y, Fukuhara S, Kunimoto S, Fukuzaki K, Sato T, Ge J, Mochizuki N, Nakaya H, Saku K, Komuro I. Conformational Switch of Angiotensin Ii Type 1 Receptor Underlying Mechanical Stress-Induced Activation. EMBO Rep. 2008;9(2):179-86. doi: 10.1038/sj.embor.7401157. PubMed PMID: 18202720; PMCID: PMC2246415.

Ye F, Wang Y, Wu C, Howatt DA, Wu CH, Balakrishnan A, Mullick AE, Graham MJ, Danser AHJ, Wang J, Daugherty A, Lu HS. Angiotensinogen and Megalin Interactions Contribute to Atherosclerosis—Brief Report. Arterioscler Thromb Vasc Biol. 2019;39(2):150-5. Epub Dec. 21, 2018. doi: 10.1161/ATVBAHA.118.311817. PubMed PMID: 30567480; PMCID: PMC6344256.

Zhou Y, Dirksen WP, Babu GJ, Periasamy M. Differential Vasoconstrictions Induced by Angiotensin Ii: Role of At1 and At2 Receptors in Isolated C57bl/6j Mouse Blood Vessels. Am J Physiol Heart Circ Physiol. 2003;285(6):H2797-803. Epub Aug. 9, 2003. doi: 10.1152/ajpheart.00466.2003. PubMed PMID: 12907424.

\* cited by examiner

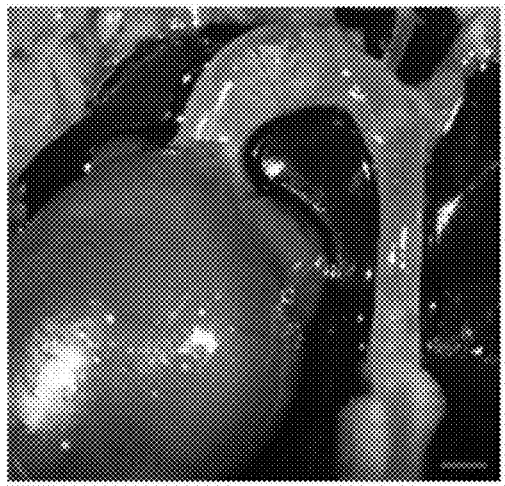
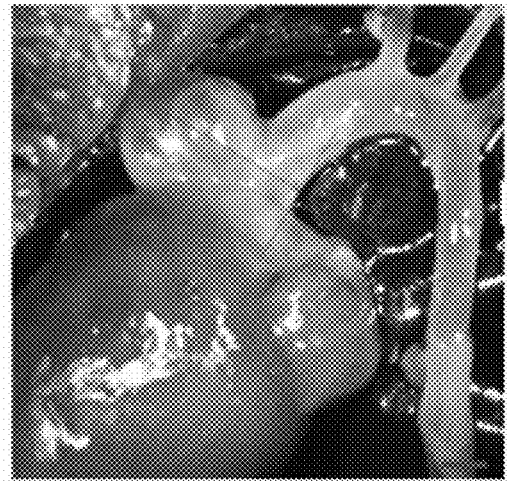
FIG. 1A  FIG. 1B
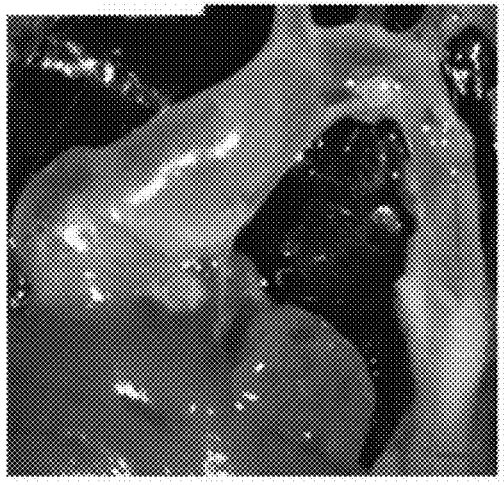
FIG. 1C

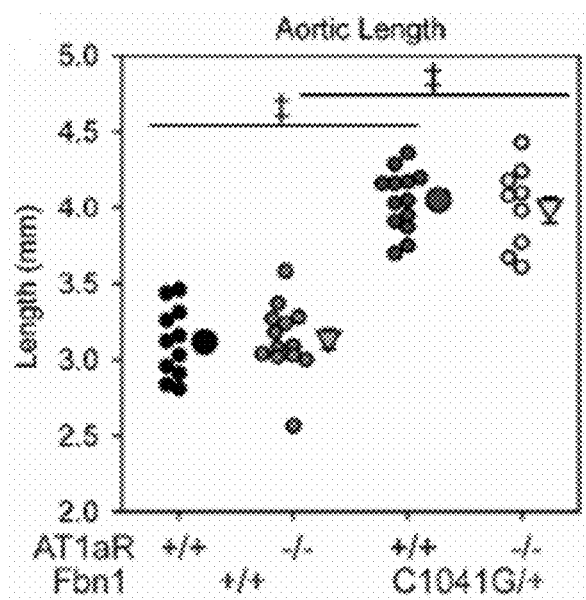
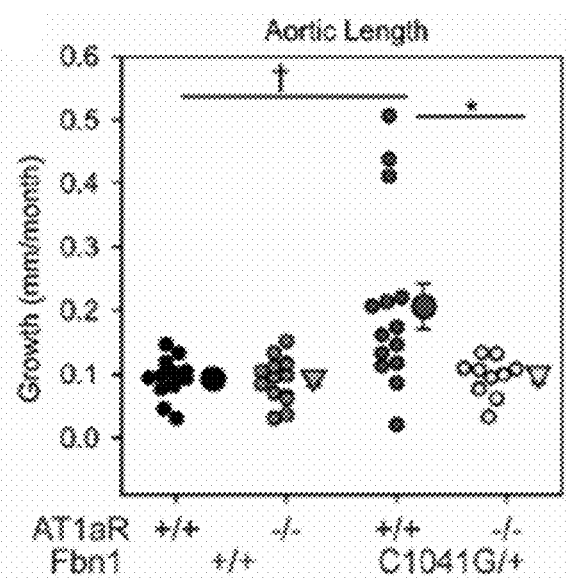
FIG. 4E
FIG. 4F

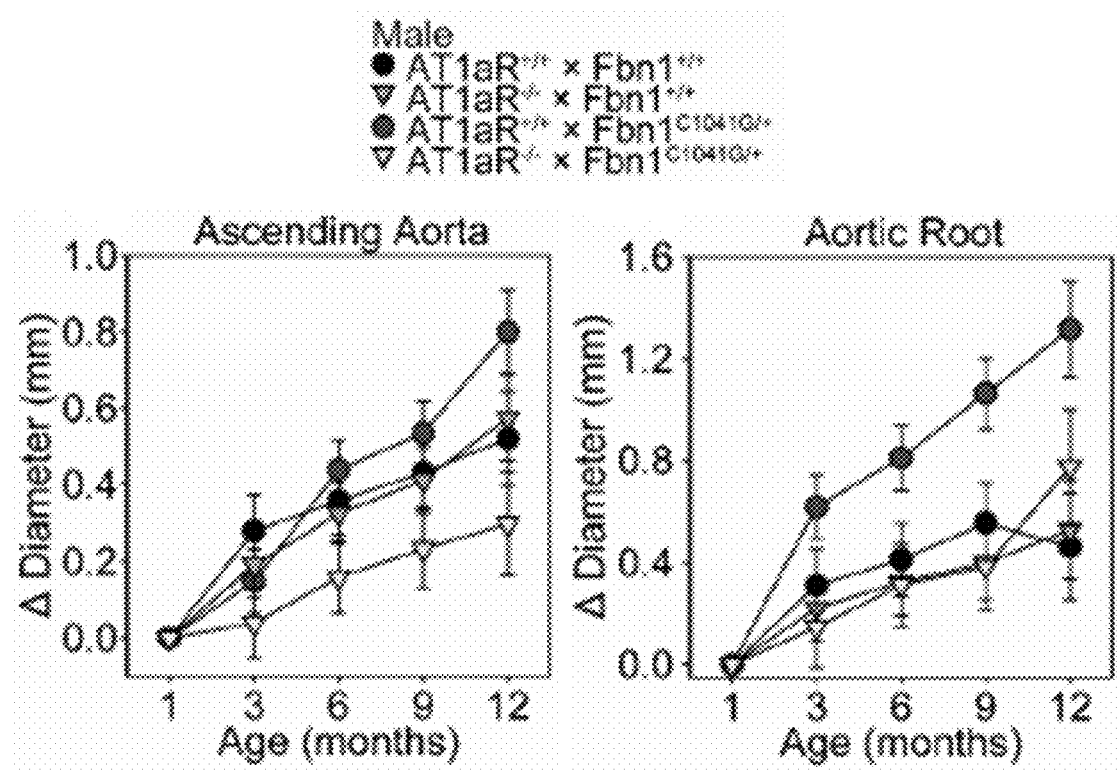
FIG. 5A
FIG. 5B
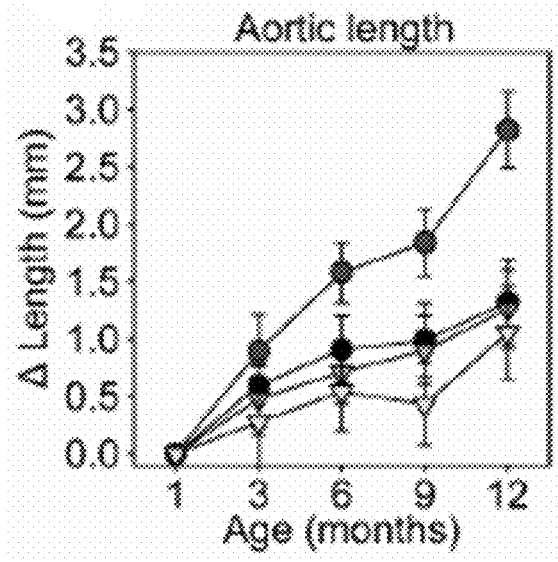
FIG. 5C

SEQUENCE LISTING

<160> NUMBER OF SEQ ID NOS: 6

<210> SEQ ID NO 1
<211> LENGTH: 16

```
<212> TYPE: DNA
<213> ORGANISM: Artificial Sequence
<220> FEATURE:
<223> OTHER INFORMATION: Synthesized

<400> SEQUENCE: 1
atcatttatt ctcggt                                                    16

<210> SEQ ID NO 2
<211> LENGTH: 20
<212> TYPE: DNA
<213> ORGANISM: Artificial Sequence
<220> FEATURE:
<223> OTHER INFORMATION: Synthesized

<400> SEQUENCE: 2
tcttccaccc tgtcacagcc                                                20

<210> SEQ ID NO 3
<211> LENGTH: 24
<212> TYPE: DNA
<213> ORGANISM: Artificial Sequence
<220> FEATURE:
<223> OTHER INFORMATION: Synthesized

<400> SEQUENCE: 3
aaatggccct taactcttct actg                                           24

<210> SEQ ID NO 4
<211> LENGTH: 22
<212> TYPE: DNA
<213> ORGANISM: Artificial Sequence
<220> FEATURE:
<223> OTHER INFORMATION: Synthesized

<400> SEQUENCE: 4
attaggaaag ggaacaggaa gc                                             22

<210> SEQ ID NO 5
<211> LENGTH: 21
<212> TYPE: DNA
<213> ORGANISM: Artificial Sequence
<220> FEATURE:
<223> OTHER INFORMATION: Synthesized

<400> SEQUENCE: 5
ctcatcattt ttggccagtt g                                              21

<210> SEQ ID NO 6
<211> LENGTH: 20
<212> TYPE: DNA
<213> ORGANISM: Artificial Sequence
<220> FEATURE:
<223> OTHER INFORMATION: Synthesized

<400> SEQUENCE: 6
gcacttgatg cacattcaca                                                20
```

INHIBITING ANGIOTENSINOGEN TO ATTENUATE AORTIC PATHOLOGY IN MARFAN SYNDROME

RELATED APPLICATIONS

This application claims priority from U.S. Provisional Application Ser. No. 63/020,324 filed May 5, 2020, the entire disclosure of which is incorporated herein by this reference.

GOVERNMENT INTEREST

This invention was made with government support under grant numbers RO1HL133723 and RO1HL139748 awarded by the National Institutes of Health. The government has certain rights in the invention.

TECHNICAL FIELD

The presently-disclosed subject matter generally relates to treatment for subjects having Marfan syndrome subjects, to reduce risks associated with aortic aneurism by inhibiting angiotensinogen (AGT). Certain embodiments of the presently-disclosed subject matter relate to inhibiting AGT using antisense oligonucleotides targeted to AGT.

INTRODUCTION

Marfan syndrome (MFS) is an autosomal dominant genetic disease caused by mutations in a large extracellular matrix protein, fibrillin-1 (FBN1). (1) It has an incidence of approximately 1:3000 live births and is associated with increased morbidity and mortality for a significant number of affected patients.

As a syndromic disorder, Marfan syndrome is characterized by a constellation of features that forms the basis of diagnosis. Thoracic aortic aneurysms (TAAs) are a key feature in Marfan syndrome that drives both diagnosis and prognosis. TAAs occur when the localized enlargement and associated weakening occurs in region of the artery that is within the thoracic or chest cavity, and increase the risk of catastrophic failure Fibrillin-1 is a protein that is necessary in the formation of elastic fibers found in connective tissue. (2) Thus, Marfan syndrome is associated abnormal connective tissue. To gain insight into the mechanisms of the disease, mice have been developed with a heterozygous expression of the C1041G mutation of the mouse fibrillin-1 protein, which is analogous to the C1039Y mutation in humans.(3) These mice have a haploinsufficiency of fibrillin-1 and mimic some pathologies present in patients with Marfan syndrome including progressive expansion of the proximal thoracic aorta.

The renin angiotensin system has been invoked as a mediator of TAA in patients with Marfan syndrome.(4) The most-extensively studied angiotensin receptor is the angiotensin II type 1 ($AT_1$) receptor. Angiotensinogen (AGT) is the only known substrate of the angiotensin proteins. AGT is cleaved to angiotensin I, which is converted by angiotensin-converting enzyme (ACE) to angiotensin II. Angiotensin II exerts a number of effects upon binding $AT_1$ receptor ($AT_1R$). Excessive angiotensin II production and $AT_1R$ stimulation have both been identified to result in hypertension.

Experimental evidence for the role of the renin angiotensin system in TAA in patients with Marfan syndrome has been based predominantly on the observation that losartan inhibits aortic pathology in mice. Losartan is classified as an angiotensin II receptor antagonist, which is indicated for treatment of hypertension.

The inhibitory effect of losartan on aortic pathology was demonstrated initially in $Fbn1^{C1041G/+}$ mice administered losartan starting at the prenatal phase of life.(5) Additionally, it has been consistently demonstrated that losartan reduces aortic expansion in many other mouse models of TAA. (6,7,8,9,10,11) However, losartan's many well-characterized effects independent of AT1 receptor antagonism potentially hinder its use as a pharmacologic tool to specifically study AT1 receptors.(12) Indeed, the benefit of losartan in inhibiting aortic root dilation in $Fbn1^{C1041G/+}$ mice has been attributed to effects such as TGF-β antagonism or nitric oxide synthase stimulation.(5,9)

Additionally, the mode by which AT1 receptors become activated in Marfan syndrome is uncertain. While activation of AT1 receptors is commonly due to engagement of the ligand, angiotensin II (AngII), the pathway can also be activated by conformational changes of the protein during cell stretch of myocytes and vascular smooth muscle cells. (13-15) This stretch activation of AT1 receptor is inhibited by pharmacological antagonists of the receptor. Based on studies in angiotensinogen deficient mice, dilated cardiomyopathy in the fibrillin-1 hypomorphic model of Marfan syndrome has been attributed to this AngII-independent activation of AT1aR.(16) The relative role of receptor activation of ligand versus stretch has not been evaluated in vascular disease.

There remains an urgent need in the art to provide effective treatments to reduce the risk of aneurysm, as well as resulting dissection and/or rupture, in patients with Marfan Syndrome.

SUMMARY

The presently-disclosed subject matter meets some or all of the above-identified needs, as will become evident to those of ordinary skill in the art after a study of information provided in this document.

A mouse model of Marfan syndrome having a mutation of fibrillin-1 protein that is analogous to the C1039Y mutation in humans was used in studies described herein. The presently-disclosed subject matter is based in part on the present inventors' discovery that deletion of the AT1a Receptor in the Marfan syndrome model attenuated aortic pathology. The presently-disclosed subject matter is based in part on the present inventors' discovery that reducing plasma concentration of angiotensinogen (AGT) in the Marfan syndrome model using an AGT antisense oligonucleotide (ASO) also resulted in attenuation of aortic pathology.

The presently-disclosed invention includes a method of attenuating aortic pathology in a subject having Marfan syndrome, which involves selecting the subject having Marfan syndrome, and administering to the subject a dose comprising an effective amount of an angiotensinogen (AGT) antisense oligonucleotide (ASO) to reduce AGT plasma levels in the subject.

In some embodiments of the method, the attenuation of aortic pathology includes reducing or inhibiting the progression of aortic dilation. In some embodiments of the method, the reduction of or inhibition of the progression of aortic dilation is in the thoracic region of the artery. In some embodiments of the method, the reduction of or inhibition of the progression of aortic dilation is in the aortic root. In some embodiments of the method, the reduction of or inhibition of the progression of aortic dilation is in the ascending aorta.

In some embodiments of the method, the attenuation of aortic pathology includes reducing the risk of thoracic aortic aneurysm (TAA). In some embodiments, the method also involves identifying the subject has having an aortic dilation.

In some embodiments, the method also involves identifying the subject as currently receiving treatment with an angiotensin receptor blocker (ARB). There are a number of known ARBs, which include, for example losartan, irbesartan, olmesartan, candesartan, valsartan, fimasartan, azilsartan, and telmisartan. In some embodiments, the ARB is concomitantly administered with the AGT ASO. In some embodiments, the method also involves administration of the AGT ASO prior to withdrawal of the ARB.

In some embodiments, the method involves administering a series of doses of AGT ASO. In some embodiments, the method involves administration of a subsequent dose of AGT ASO about 7 days after the previous dose. In some embodiments, the method involves administration of a subsequent dose of AGT ASO about 14 days after the previous dose. The administration of the AGT ASO can be, for example, by parenteral administration.

In some embodiments of the method, the subject is human. In some embodiments, the subject is male. In some embodiments of the method, initiation of treatment occurs with the subject is younger than sixteen-years-old.

In some embodiments of the method, the AGT ASO comprises a sequence selected from the group consisting of SEQ ID NOS: 1 and 2. (SEQ ID NO: 1: ATCATTTATTCTCGGT; ION No: 1095847; Chemistry: 3-10-3 (S)-cEt gapmer w/phosphorothioate backbone; SEQ ID NO: 2: TCTTCCACCCTGTCACAGCC). In some embodiments of the method, the AGT ASO is modified with N-Acetylgalactosamine (GalNAc).

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are used, and the accompanying drawings of which:

FIGS. 1A-1C. Regional heterogeneity of thoracic aortic aneurysm (TAA) in $Fbn1^{C1041G/+}$ mice. TAAs in one year old $Fbn1^{C1041G/+}$ mice have a variable phenotype of pathology location. Examples include aneurysmal presence in; A) ascending aorta only (FIG. 1A), aortic root only (FIG. 1B), or both segments (FIG. 1C). Bar in lower left corner=1 mm.

FIG. 3A includes representative ultrasound images of the thoracic aorta in male $AT1aR^{+/+} \times Fbn1^{+/+}$, $AT1aR^{-/-} \times Fbn1^{+/+}$, $AT1aR^{+/+} \times Fbn1C1041G/+$, and $AT1aR^{-/-} \times Fbn1^{C1041G/+}$ mice. Bar in lower left corner=1 mm. Sequential ultrasound measurements of the ascending aorta (FIG. 3B), aortic root (FIG. 3C), and aortic length (FIG. 3D). * $p<0.05$ of $AT1aR^{+/+} \times Fbn1^{+/+}$ versus $AT1aR^{+/+} \times Fbn1C1041G/+$; † $p<0.05$ of $AT1aR^{+/+} \times Fbn1^{C1041G/+}$ versus $AT1aR^{-/-} \times Fbn1C1041G/+$; n=11-15/group. FIG. 3E includes representative in situ images of the thoracic aorta. Bar in lower left corner=1 mm. FIG. 3F includes measurement of in situ aortic dimensions taken at the maximal aortic diameter. † $p<0.01$; ‡ $p<0.001$; n=10-15/group.

FIGS. 4A-4F. Aortic dimensions at 1 month of age and aortic growth in male mice. Presented are data including ultrasound measurements of the ascending aorta (FIG. 4A), aortic root (FIG. 4C), and aortic length (FIG. 4E) in diastole at 1 month of age from male $AT1aR^{+/+} \times Fbn1^{+/+}$, $AT1aR^{-/-} \times Fbn1^{+/+}$, $AT1aR^{+/+} \times Fbn1C1041G/+$, and $AT1aR^{-/-} \times Fbn1C1041G/+$ mice. Mean monthly growth is presented, including ascending aorta growth (FIG. 4B), aortic root growth (FIG. 4D), and aortic length growth (FIG. 4F) from 1 month to 12 months in male $AT1aR^{+/+} \times Fbn1^{+/+}$, $AT1aR^{-/-} \times Fbn1^{+/+}$, $AT1aR^{+/+} \times Fbn1C1041G/+$, and $AT1aR^{-/-} \times Fbn1C1041G/+$ mice. * $p<0.05$, † $p<0.01$, ‡ $p<0.001$; n=11-15/group.

FIGS. 5A-5C. Growth from 1 month of age in male AT1aR deficient, Fbn1C1041G/+ mice. Data are represented as change in dimensions over the measurement at 1 month of age of the ascending aorta (FIG. 5A), aortic root (FIG. 5B), and aortic length (FIG. 5C). * $p<0.05$ of $AT1aR^{+/+} \times Fbn1C1041G/+$ versus $AT1aR^{-/-} \times Fbn1C1041G/+$; n=11-11/group.

FIG. 6A includes systolic blood pressure measured by a tail cuff based technique in 12 month old male mice. * $p<0.05$, † $p<0.01$, ‡ $p<0.001$; n=5-10/group. FIG. 6B includes sequential body weight of male mice. FIG. 6C includes correlation between systolic blood pressure and aortic diameters at 12 months of age between male mice. n=5-10/group. Black circle=$AT1aR^{+/+} \times Fbn1^{+/+}$, grey triangle=$AT1aR^{-/-} \times Fbn1^{+/+}$, dart grey circle=$AT1aR^{+/+} \times Fbn1C1041G/+$, and white triangle=$AT1aR^{-/-} \times Fbn1C1041G/+$.

FIG. 9F includes low magnification images of aortic sections stained with Verhoeff elastin stain in 12 month old male AT1aR$^{+/+}$×Fbn1$^{+/+}$, AT1aR$^{-/-}$×Fbn1$^{+/+}$, AT1aR$^{+/+}$×Fbn1C1041G/+, and AT1aR$^{-/-}$×Fbn1C1041G/+ mice. FIG. 9G includes low magnification images of aortic sections stained with Verhoeff elastin stain in 8 month old male Fbn1C1041G/+ mice after 6 months of control antisense oligonucleotide (ASO) or angiotensinogen (AGT) ASO.

FIG. 10A includes representative images of Verhoeff's elastin staining in ascending aortic sections from male AT1aR$^{+/+}$×Fbn1$^{+/+}$, AT1aR$^{-/-}$×Fbn1$^{+/+}$, AT1aR$^{+/+}$×Fbn1C1041G/+, and AT1aR$^{-/-}$×Fbn1C1041G/+ mice. Bar in lower left corner=100 FIG. 10B presents the number of breaks per high powered field detected in aortic sections. FIG. 10C presents the medial thickness as measured by the distance between the inner elastic lamina and external elastic lamina in aortic sections. * $p<0.05$, ‡ $p<0.001$; n=5/group.

FIG. 11A depicts the study design and administration schedule of ASOs in male Fbn1C1041G/+ mice. A loading dose of control ASO or AGT ASO (80 mg/kg) was administered day 1 and 4 of study. Maintenance doses of control ASO or AGT ASO (40 mg/kg) was administered every 7 days. Presented are a Western blot of plasma AGT (FIG. 11B) and total plasma protein (FIG. 11C) in 8 month old male Fbn1C1041G/+ mice administered either control ASO or AGT ASOs. Blot represents one of two experiments. ‡ $p<0.001$; n=6/group. Representative ultrasound (FIG. 11D) and in situ images (FIG. 11E) of aortas from 8 month old Fbn1C1041G/+ mice administered either control ASO or AGT ASO. Bar in lower left corner=1 mm. Sequential ultrasound measurements of the ascending aorta (FIG. 11F), aortic root (FIG. 11G), and aortic length (FIG. 11H) in diastole from 2 months to 8 months of age in male Fbn1$^{C1041G/+}$ mice dosed with either control ASO or AGT ASO. * $p<0.05$, † $p<0.01$, ‡ $p<0.001$; n=8-10/group.

FIG. 13A includes representative images of Verhoeff's elastin staining in aortic sections from male Fbn1$^{C1041G/+}$ mice administered either control ASO or AGT ASO for 6 months. Bar in lower left corner=100 μm. FIG. 13B presents the number of breaks per high powered field detected in aortic sections. FIG. 13C presents the medial thickness as measured by the distance between the inner elastic lamina and external elastic lamina in aortic sections. † $p<0.01$, ‡ $p<0.001$; n=5/group.

FIG. 15A presents the survival probability as a function of time for Fbn1$^{mgR/mgR}$ males administered losartan at P25 and P50. FIG. 15B presents the results of a survival analysis starting at P50 to control for non-rupture deaths and humane endpoints. Losartan at P50 improves survival versus controls (* $p<0.05$, *** $p<0.001$ by log rank analysis).

DESCRIPTION OF EXEMPLARY EMBODIMENTS

Figure 2A:
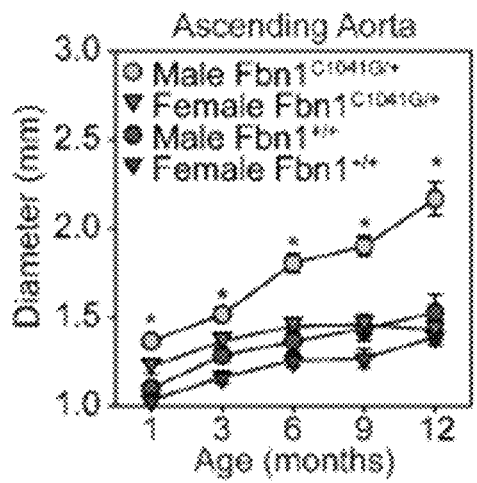
FIGS. 2A-2F. TAA in $Fbn1^{C1041G/+}$ mice is sexually dimorphic. Sequential ultrasound measurements of the ascending aorta (FIG. 2A), aortic root (FIG. 2B), and aortic length (FIG. 2C) in diastole from 1 month to 12 months of age of male and female $Fbn1^{+/+}$ and $Fbn1^{C1041G/+}$ mice. Data represented as change in dimensions over baseline at 1 month of age of the ascending aorta (FIG. 2D), aortic root (FIG. 2E), and aortic length (FIG. 2F). * $p<0.05$ of male $Fbn1^{C1041G/+}$ versus female $Fbn1^{C1041G/+}$ mice; n=9-15/group.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

The presently-disclosed subject matter relates to a method for attenuating aortic pathology in a subject having Marfan syndrome by reducing angiotensinogen plasma levels in the subject. Marfan syndrome is characterized by a risk of aortic pathology, including aortic enlargement or dilation, often assessed by measuring dimensions of the aorta, including the diameter. A normal diameter for an aorta is considered to be about 2.6-2.9 cm. When a portion of the aorta is greater than 3 cm it is considered dilation. Medical intervention is often considered when the diameter extends beyond 4 cm, or beyond 4.5 cm, or beyond 5.5 cm. A localized enlargement can create a weakening in the aortic wall, increasing the risk of catastrophic failure, and can be referred to as an aortic aneurysm. Thoracic aortic aneurysms (TAA) are particularly associated with Marfan syndrome, and can occur in the aortic root, the ascending aorta, or the descending thoracic aorta.

The presently-disclosed subject matter relates to a method of attenuating aortic pathology in a subject having Marfan syndrome, which involves selecting the subject having Marfan syndrome, and administering to the subject a dose comprising an effective amount of an angiotensinogen (AGT) antisense oligonucleotide (ASO) to reduce AGT plasma levels in the subject.

As used herein, the term "administering" refers to providing an agent to a subject, and includes, but is not limited to administering by a medical professional and self-administering. As used here, an "effective amount" refers to an amount sufficient to effectuate a reduction in circulating (or plasma concentration of) AGT in a subject. The effective amount can vary among subjects depending on the health and physical condition of the subject to be treated, the taxonomic group of the subject to be treated, the formulation of the composition, assessment of the subject's medical condition, and other relevant factors.

In some embodiments of the method, the attenuation of aortic pathology includes reducing or inhibiting the progression of aortic dilation. In some embodiments of the method, the reduction of or inhibition of the progression of aortic dilation is in the thoracic region of the artery. In some embodiments of the method, the reduction of or inhibition of the progression of aortic dilation is in the aortic root. In some embodiments of the method, the reduction of or inhibition of the progression of aortic dilation is in the ascending aorta. In some embodiments of the method, the attenuation of aortic pathology includes reducing the risk of thoracic aortic aneurysm (TAA). In some embodiments, the method also involves identifying the subject has having an aortic dilation.

As used herein, the term "attenuate" refers to a reduction in aortic pathology or a beneficial therapeutic effect in connection with aortic pathology in a subject having Marfan syndrome. As used herein, the terms "treatment" or "therapeutic effect" relate to any treatment of aortic pathology that is associated with Marfan syndrome, including but not limited to treatment to prevent development, reduce the severity, and/or inhibit the progression of aortic pathology (e.g., development of aortic expansion, dilation, increased dimensions such as diameter, aneurysm, dissection, rupture). In this regard, in is understood that treatment to prevent or inhibit an outcome does not necessarily refer to a total elimination of any sign of the outcome, but rather to a reduction of risk and/or severity.

The presently-disclosed subject matter is based in part on the present inventors' discovery that deletion of the AT1a Receptor in the Marfan syndrome model attenuated aortic pathology. The presently-disclosed subject matter is based in part on the present inventors' discovery that reducing plasma concentration of angiotensinogen (AGT) in the Marfan syndrome model using an AGT antisense oligonucleotide (ASO) also resulted in attenuation of aortic pathology, noting that AGT is the only known substrate of angiotensin II, the natural ligand of the AT1a Receptor.

In this regard, the invention relates to discoveries in connection what Marfan syndrome, to which any known AGT ASO can be applied. Various AGT ASOs are known in the art for use in inhibiting AGT, and can be used in connection with the presently-disclosed invention.

For example, an AGT ASO could be selected from among those identified in U.S. Pat. No. 10,912,792 for "Compounds and Methods for Modulating Angiotensinogen Expression", U.S. Pat. No. 10,709,728 for "Polynucleotide Agent Targeting Angiotensinogen (AGT) and Methods of Use Thereof", and U.S. Patent Application Publication No. 2015/0297629 for "Modulation of Renin-Angiotensin System (RAS) Related Diseases by Angiotensinogen", each of which is incorporated herein by this reference.

In some embodiments, the AGT ASO can comprise the sequence of SEQ ID NO: 1 or SEQ ID NO: 2, as disclosed herein, or a complement thereof. (SEQ ID NO: 1: ATCATTTATTCTCGGT; ION No: 1095847; Chemistry: 3-10-3 (S)-cEt gapmer w/phosphorothioate backbone; SEQ ID NO: 2: TCTTCCACCCTGTCACAGCC).

As will be appreciated, there are also a number of known modifications, formulations, compositions, delivery systems and the like for use in connection with administration of AGT ASOs, which can be applied to the presently-disclosed subject matter. For example, in some embodiments, the AGT ASO can be modified with N-Acetylgalactosamine (GalNAc)

As those of ordinary skill in the art will appreciate, certain subjects having Marfan syndrome are administered a angiotensin receptor blocker (ARB), such as losartan. Aspects of the presently-disclosed invention are also related to the present inventors' discoveries as they relate to use of ARB in Marfan syndrome. In particular, as described herein, it was found that losartan increases survival of the Fbn1$^{mgR/mgR}$ mouse model of Marfan syndrome in an age-dependent manner. As is also described herein, it was discovered that losartan does not improve survival in fibrillin-1 hypomorphic mice with established aortic aneurysm. Furthermore, as also disclosed herein, it was discovered that there was increased death due to aortic rupture in a Marfan syndrome mouse model within 30 days of losartan withdrawal. Additionally, as disclosed herein, it was discovered that AGT ASOs result in a sustained reduction in circulating AGT for days after administration.

With cumulative consideration to these results, the presently-disclosed subject matter includes embodiments involving co-administration or concomitant administration of an ARB and an AGT ASO, to confer the benefits of associated with both the ARB and AGT ASO, with further consideration potential drawbacks and/or risks associated with the ARB. In some embodiments, the method can further involve a step of identifying the subject as currently receiving treatment with an ARB, or the step of administering AGT ASO, such that the subject is receiving both an ARB or an ASO. In some embodiments the method involves concomitantly administering an ARB with the AGT ASO. As used herein, the term "co-administration" refers administration of two or more active agents to a subject. The two or more agents can be in a single composition, or can be in separate compositions. Each of the two or more agents can be administered through the same or different routes of administration. Co-administration encompasses concomitant, parallel, or sequential administration. As used herein, the term "concomitant administration" refers to the co-administration of two agents in any manner in which the effects of both are manifest in the subject. Concomitant administration does not require that both agents be administered in a single composition, in the same dosage form, or by the same route of administration. The effects of both agents need not manifest themselves at the same time. The effects need only be overlapping for a period of time and need not be coextensive.

In some embodiments, the method also involves initiating administration of the AGT ASO prior to withdrawal of ARB.

In some embodiments, after administration of AGT ASO is initiated, co-administration with ARB is continued for at least about 1, 2, 3, 4, 5, 6, 7, 8, 9, 10, 15, 20, 25, or 30 days before withdrawal of the ARB, while administration of AGT ASO is continued. In some embodiments, the ARB is losartan, irbesartan, olmesartan, candesartan, valsartan, fimasartan, azilsartan, or telmisartan.

In some embodiments of the presently-disclosed subject matter, the method involves administering a series of doses of AGT ASO. With regard to the disclosure herein that the reduced level of circulating AGT persist following administration of AGT ASO, in some embodiments, the method involves administering a subsequent dose 1, 2, 3, 4, 5, 6, 7, 8, 9, 10, 11, 12, 13, or 14 days after the previous dose. For example, in some embodiments, doses can be administered every week or every two weeks.

As used herein, the term "dose" refers to a specified quantity of an agent provided in a single administration, or in a specified time period. In certain embodiments, a dose can be administered in one, two, or more units of administration. For example, in certain embodiments where subcutaneous administration is desired, the desired dose requires a volume not easily accommodated by a single injection, therefore, two or more injections may be used to achieve the desired dose. In certain embodiments, the agent is administered by infusion over an extended period of time or continuously.

In accordance with the methods disclosed herein, the AGT ASO can be administered in a number of ways. In certain embodiments, the AGT ASO is administered parenterally. Parenteral administration includes, but is not limited to, intravenous, intra-arterial, subcutaneous, intraperitoneal, intraocular, intramuscular, intracranial, intrathecal, intramedullary, intraventricular or intratumoral injection or infusion. Parenteral administration also includes intranasal administration. In some embodiments, parenteral administration is by infusion. Infusion can be chronic or continuous or short or intermittent. In some embodiments, parenteral administration is by injection.

As used herein, the terms "subject" or "patient" refer to a human or non-human animal selected for treatment. In some embodiments, the subject is male. In some embodiments, the subject is female. In some embodiments the subject is younger than 15, 16, 17, 18, 19, 20, 21, 22, 23, 24, 25, 26, 27, 28, 29, 30, 31, 32, 33, 34, 35, 36, 37, 38, 39, or 40 years old. In some embodiments the subject is 12 years old to 15, 16, 17, 18, 19, 20, 21, 22, 23, 24, 25, 26, 27, 28, 29, 30, 31, 32, 33, 34, 35, 36, 37, 38, 39, or 40 years old.

While the terms used herein are believed to be well understood by those of ordinary skill in the art, certain definitions are set forth to facilitate explanation of the presently-disclosed subject matter.

Unless defined otherwise, all technical and scientific terms used herein have the same meaning as is commonly understood by one of skill in the art to which the invention(s) belong.

All patents, patent applications, published applications and publications, GenBank sequences, databases, websites and other published materials referred to throughout the entire disclosure herein, unless noted otherwise, are incorporated by reference in their entirety.

Where reference is made to a URL or other such identifier or address, it understood that such identifiers can change and particular information on the internet can come and go, but equivalent information can be found by searching the internet. Reference thereto evidences the availability and public dissemination of such information.

As used herein, the abbreviations for any protective groups, amino acids and other compounds, are, unless indicated otherwise, in accord with their common usage, recognized abbreviations, or the IUPAC-IUB Commission on Biochemical Nomenclature (See, Biochem. (1972) 11(9): 1726-1732).

Although any methods, devices, and materials similar or equivalent to those described herein can be used in the practice or testing of the presently-disclosed subject matter, representative methods, devices, and materials are described herein.

In certain instances, nucleotides and polypeptides disclosed herein are included in publicly-available databases, such as GENBANK® and SWISSPROT. Information including sequences and other information related to such nucleotides and polypeptides included in such publicly-available databases are expressly incorporated by reference. Unless otherwise indicated or apparent the references to such publicly-available databases are references to the most recent version of the database as of the filing date of this Application.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, in some embodiments ±0.1%, in some embodiments ±0.01%, and in some embodiments ±0.001% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, "optional" or "optionally" means that the subsequently described event or circumstance does or does not occur and that the description includes instances where said event or circumstance occurs and instances where it does not. For example, an optionally variant portion means that the portion is variant or non-variant.

The presently-disclosed subject matter is further illustrated by the following specific but non-limiting examples. The following examples may include compilations of data that are representative of data gathered at various times during the course of development and experimentation related to the present invention.

EXAMPLES

Example 1: Mice

Studies were performed in accordance with recommendations for design and reporting of animal aortopathy studies.(17, 18) Studies were performed using littermate controls. Mice and genealogy were tracked with Mosaic Vivarium Laboratory Animal Management Software (Virtual Chemistry). Male and female AT1aR deficient (AT1aR$^{-/-}$) (stock #002682) and Fbn1$^{C1041G/+}$ (stock #012885) mice were obtained from The Jackson Laboratory. Male AT1aR heterozygous (AT1aR+/−)×Fbn1$^{C1041G/+}$ were bred with female AT1aR+/−×fibrillin-1 wild type (Fbn1$^{+/+}$) mice to generate four experimental groups per sex: male and female AT1aR wild type (AT1aR$^{+/+}$)×Fbn1$^{+/+}$, AT1aR$^{-/-}$×Fbn1$^{+/+}$, AT1aR$^{+/+}$×Fbn1$^{C1041G/+}$ and AT1aR$^{-/-}$×Fbn1$^{C1041G/+}$ mice. Littermates were separated by sex and genotypes and were randomized when housing mice after weaning. For AGT ASO experiments, 2-month-old male Fbn1$^{C1041G/+}$ mice were procured from The Jackson Laboratory and randomized into experimental groups using a random number generator. Mice were checked daily for health, and necropsy was performed to adjudicate cause of death. Mice were housed up to 5 per cage and maintained on a 14:10 hour light:dark cycle. Mice were fed Teklad Irradiated Global 18% Protein Rodent Diet #2918 ad libitum and allowed ad libitum access to water via a Lixit system. Bedding was provided by P. J. Murphy (Coarse SaniChip) and changed weekly during the study. Cotton pads were provided as enrichment. The room temperature was maintained at 21° C. and room humidity was maintained at 50%. All protocols were approved by University of Kentucky IACUC.

Example 2: Genotyping

Mice were genotyped twice using tail tissue. Group allocation was based on genotyping performed after weaning at postnatal day 28 and again after study termination to verify genotypes. AT1aR deletion was assayed using forward primer 5'-AAATGGCCCTTAACTCTTCTACTG-3' (SEQ ID NO: 3) and reverse primer 5'-ATTAGGAAAGG-GAACA GGAAGC-3' (SEQ ID NO: 4) covering a neo cassette that disrupts AT1aR spanning bps 110-635. The neo cassette removed approximately 0.5 kb and inserted approximately 1 kb of neo gene. AT1aR$^{+/+}$ generated a 631 bp product. AT1aR$^{-/-}$ generated a ~1.1 kbp product. Fbn1$^{C1041G/+}$ was assayed using forward primer 5'-CTCAT-CATTTTTGGCCAGTTG-3' (SEQ ID NO: 5) and reverse primer 5'-GCACTTGATGCACATTCACA-3' (SEQ ID NO: 6) covering a single loxP intronic sequence within intron 24 which should not exist in wild type mice. The protocol used was as described by The Jackson Laboratory. Fbn1$^{+/+}$ generates a 164 bp product. Fbn1$^{C1041G/+}$ generates a 212 bp product. Post-termination validation genotyping was performed by Transnetyx.

Example 3: Antisense Oligonucleotides

Scrambled control ASO (#549149) and AGT ASO (#109547) were provided by Ionis Pharmaceuticals. Lyophilized ASOs were diluted in PBS as recommended by the manufacturer. Mice were randomized to study group using a random number generator. Two-month-old male Fbn1$^{C1041G/+}$ mice were administered control ASO or AGT ASO (80 mg/kg) subcutaneously at day 1 and 3 of study. Mice were maintained on subcutaneous control ASO or AGT ASO (40 mg/kg) every 7 days for the remainder of the study.

Example 4: Ultrasound Measurements

Ultrasound was performed by standardized protocols that have been as described previously.(19, 20, 21) Briefly, mice were anesthetized using inhaled isoflurane (2-3% vol/vol) and maintained at a heart rate of 450-550 beats per minute during image capture to reduce anesthesia exposure and maintain consistent heart rate between animals (Somnosuite, Kent Scientific). The order by which mice were subject to ultrasound was randomized. Ultrasound images were captured using a Vevo 3100 system with a 40 MHz transducer (Visualsonics). Images captured were standardized according to two anatomical landmarks: the innominate artery branch point and aortic valves. The largest luminal ascending aortic diameter between the sinotubular junction and the innominate artery were measured in end-diastole over three cardiac cycles by two independent observers.

Example 5: Measurement of In Situ Aortic Diameters

Mice were terminated by overdose of ketamine:xylazine followed by cardiac puncture and saline perfusion. The order in which mice were taken down was randomized. Aortas were dissected away from surrounding tissue and Optimal Cutting Temperature Compound (Sakura Finetek) was introduced into the left ventricle to maintain aortic patency. A black plastic sheet was inserted beneath the aorta and heart to increase contrast and facilitate visualization of aortic borders. Aortas were imaged using a Nikon SMZ800 stereoscope and measurements were recorded using NIS-Elements AR 4.51 software (Nikon Instruments Inc.). Ascending aortic diameters were measured at the largest width perpendicular to the vessel.

Example 6: Histology

Mice were ranked according to their ascending aortic diameter by ultrasound, and the median five per group were selected for histology. Tissue sections (10 µm) were acquired from the aortic root to the aortic arch at 100 µm intervals using a cryostat. The section corresponding to a region of maximal dilation between the sinotubular junction and the arch was analyzed. Elastin fragmentation was visualized by Verhoeff elastin staining under 20× magnification and images from three high powered fields per section were recorded for analysis. Individual data were represented as the mean of three high power fields. Fragmentation was defined as the presence of discernable breaks of continuous elastic lamina. Medial thickness was measured at the greatest thickness from inner to external elastic laminae in 3 images using NIS-Elements AR software. Measurements were verified by an independent investigator who was blinded to sample identification.

Example 7: AGT Western Blotting

Reducing buffer (Bio-Rad 161-0737 and Sigma M7522) and plasma (0.3 µL) from mice administered control or AGT ASO were heated to 95° C. for 5 minutes. Samples were fractionated on an SDS-PAGE gel (10% wt/vol; Bio-Rad 456-8033). Proteins were transferred to a PVDF membrane via Trans-blot system (Bio-Rad 170-4256). Total proteins were detected by Ponceau S. Membranes were blocked by milk (5% wt/vol; Bio-Rad 170-6404) in TBS-T (0.1% wt/vol). Membranes were then incubated with antibodies against total AGT (0.1m/mL; IBL 28101) for 1 hour at room temperature then with HRP-conjugated goat-antirabbit IgG (0.2 µg/mL; Vector Pi-1000). Membranes were developed with Clarity Max ECL (Bio-Rad 1705064) on a ChemDoc MP system. Blots were quantified using Bio-Rad CFX software.

Example 8: Statistics

All animals that met pre-specified inclusion criteria, and were not excluded due to death by humane endpoint unrelated to aortic disease (fighting, infection), had cause of death adjudicated by necropsy. Statistical analyses were performed using SigmaPlot 14.0. Equal variance and normality of data determined whether non-linear, logarithmic transformation was performed and whether parametric or non-parametric tests were used. Two-way ANOVA or Student's t-test was performed for parametric comparisons; Holm-Sidak was used for post-hoc tests. Kruskal-Wallis or Rank Sum was performed for non-parametric comparisons with Dunn's method for post hoc tests. Data are represented as individual data points, mean±SEM, or as box and whisker plots representing median and interquartile range where applicable.

Figure 2B:
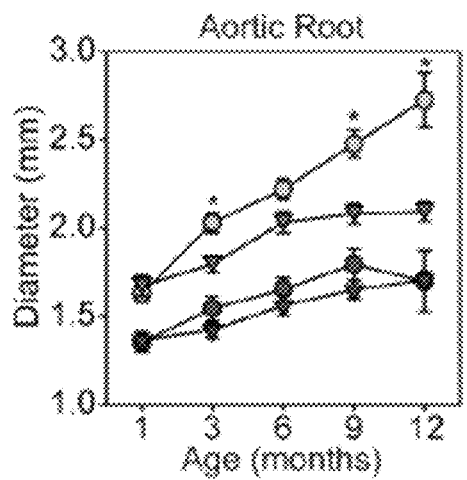
Figure 2C:
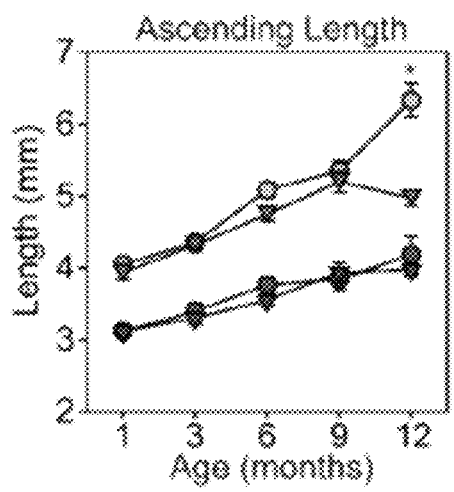
Figure 2D:
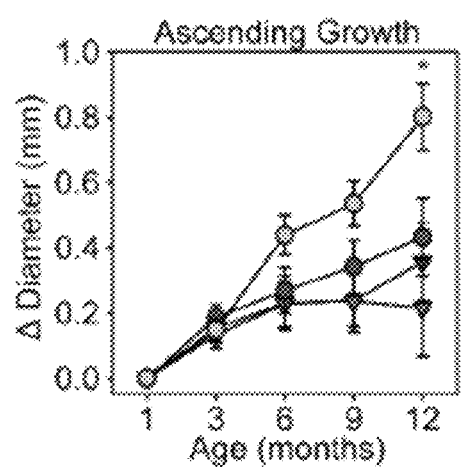
Figure 2E:
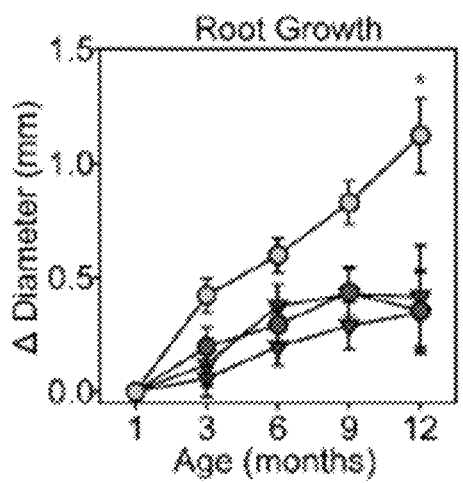
Figure 2F:
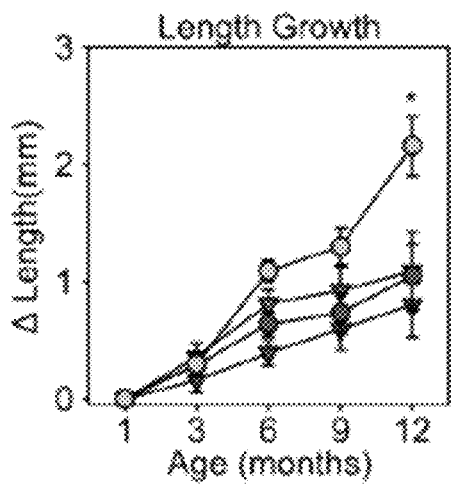

Example 9: Progression of Aortic Dimensions Sexually Dimorphic in $Fbn1^{C1041G/+}$ Mice In initial studies, the progression of aortic diameters over a 12-month interval was determined in both male and female $Fbn1^{+/+}$ and $Fbn1^{C1041G/+}$ mice. Because TAA in $Fbn1^{C1041G/+}$ mice has variable pathology within the proximal thoracic aorta, several parameters were measured (FIG. 1). This included the ascending aortic diameter, aortic root diameter, and ascending aortic length. In $Fbn1^{+/+}$ mice, there was no statistical difference in the ascending aorta diameter, aortic root diameter, or ascending aortic length between female and male at any interval up to 12 months of age (FIGS. 2A-2C). At one month of age, aortic root diameters and ascending aortic lengths were increased in both male and female $Fbn1^{C1041G/+}$ mice compared to $Fbn1^{+/+}$ mice. However, only male $Fbn1^{C1041G/+}$ mice exhibited statistically significant ascending aortic dilation compared to sex-matched littermates at one month of age. Despite differences at 1 month of age in female mice, the subsequent increase in diameter of ascending aorta and aortic root, and length of the ascending region were not statistically different between $Fbn1^{+/+}$ and $Fbn1^{C1041G/+}$ mice (FIGS. 2D-2F). In contrast, male $Fbn1^{C1041G/+}$ mice had augmented increases in diameters of ascending aorta and aortic root and ascending aortic length, compared to male $Fbn1^{+/+}$ littermates over the course of 12 months. Since female $Fbn1^{C1041G/+}$ mice had no significant differences in the progression of aortic dimensions compared to their wild type littermates, subsequent experiments used predominantly male mice.

In another study conducted in the fibrillin-1 hypomorphic (FBN1$^{mgR/mgR}$) mouse model of syndromic TAA, it was found that AngII-induced TAA in mice was exacerbated by ovariectomy of female mice and ameliorated by orchiectomy of male mice (Data not shown). This effect was not seen in female or male mice with established TAA (Data not shown). These data indicate that endogenous estrogens are protective against and endogenous androgens are detrimental to the development of TAA but may have limited effect on reversing established, syndromic TAA.

Figure 3A:
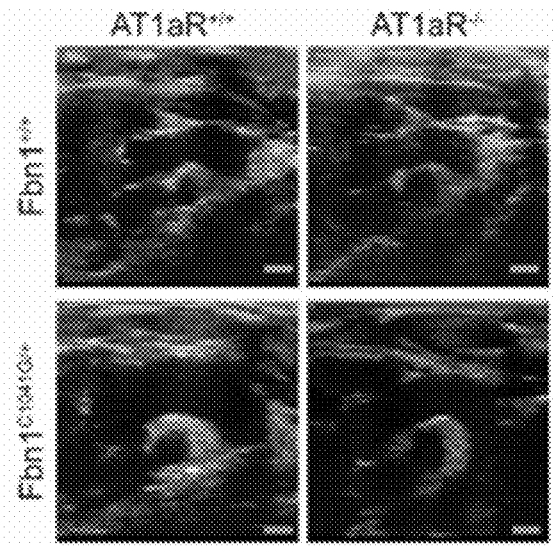
FIGS. 3A-3F. AT1aR deletion attenuated ascending aortic dilation in male $Fbn1^{C1041G/+}$ mice.

Example 10: AT1aR Deletion Attenuated Aortic Pathology in Male $Fbn1^{C1041G/+}$ Mice To study the effects of AT1aR on aortic dilation in $Fbn1^{C1041G/+}$ mice, $Fbn1^{C1041G/+}$ mice that were either AT1aR$^{+/+}$ or AT1aR$^{-/-}$ were generated. $Fbn1^{C1041G/+}$ mice were also compared against $Fbn1^{+/+}$ mice that were also either AT1aR$^{+/+}$ or AT1aR$^{-/-}$. Aortic dimensions were measured using ultrasound images acquired from a right parasternal view at diastole (FIG. 3A). Images were acquired from every mouse at the stated intervals up to 12 months of age, with no deaths of any cause occurring during the study.

Figure 3B:
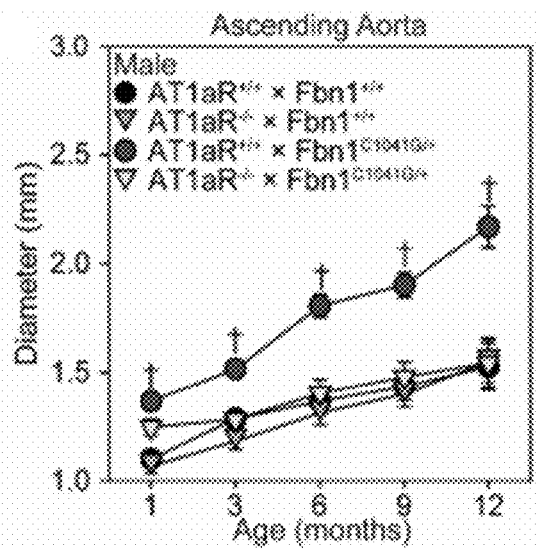
Figure 3C:
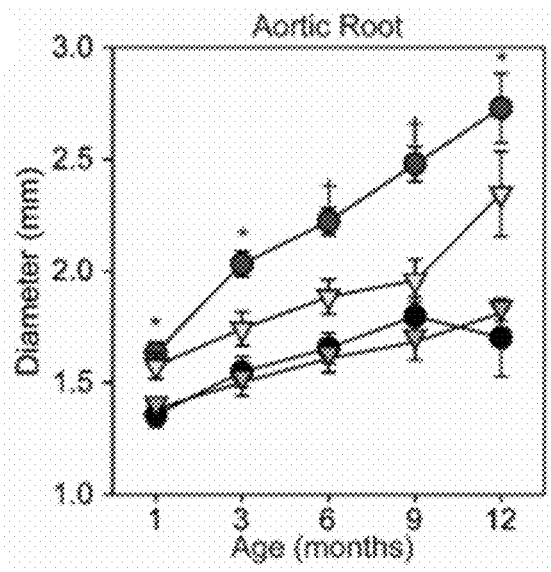
Figure 3D:
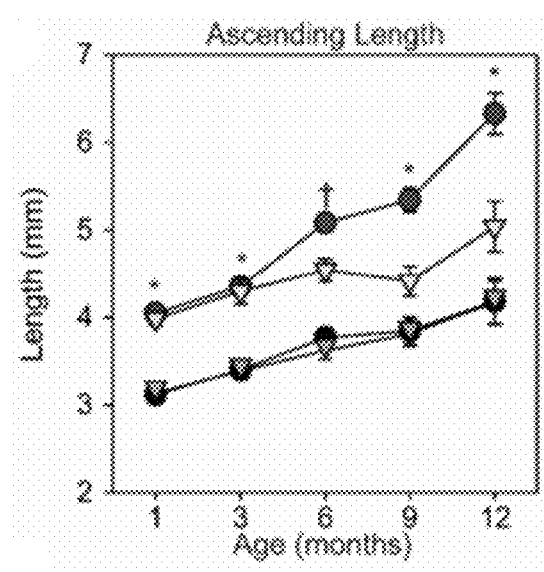
Figure 3E:
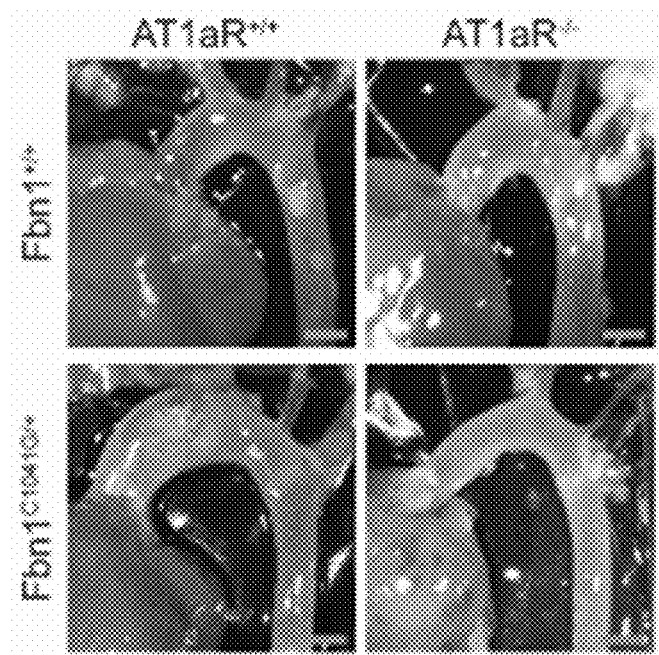
Figure 3F:
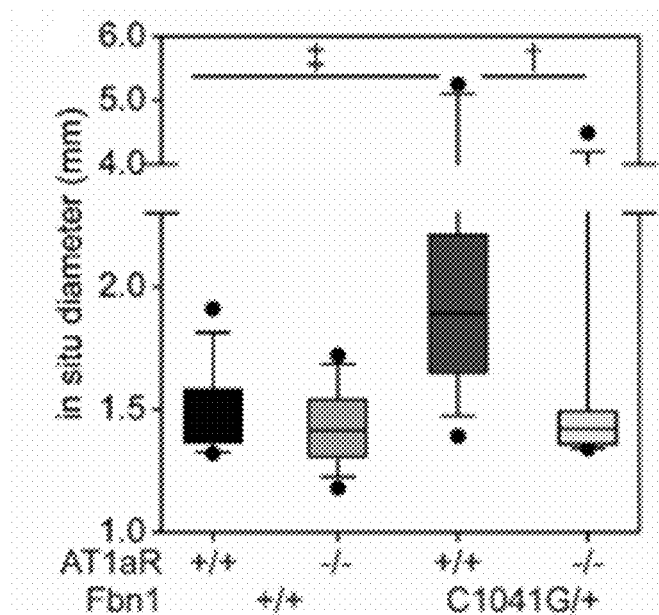
Figure 4A:
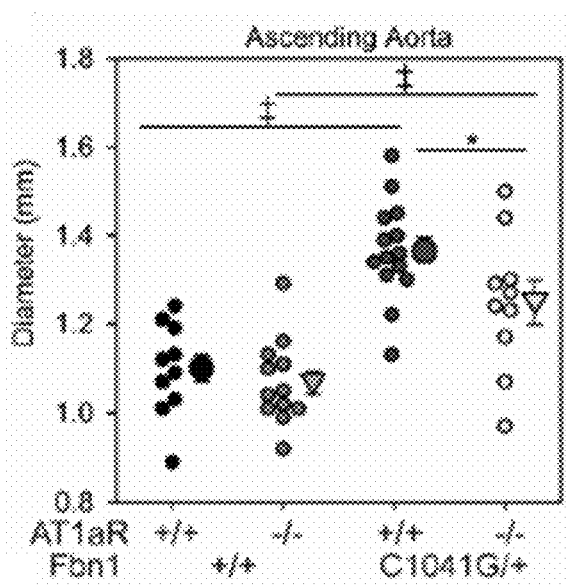
Figure 4B:
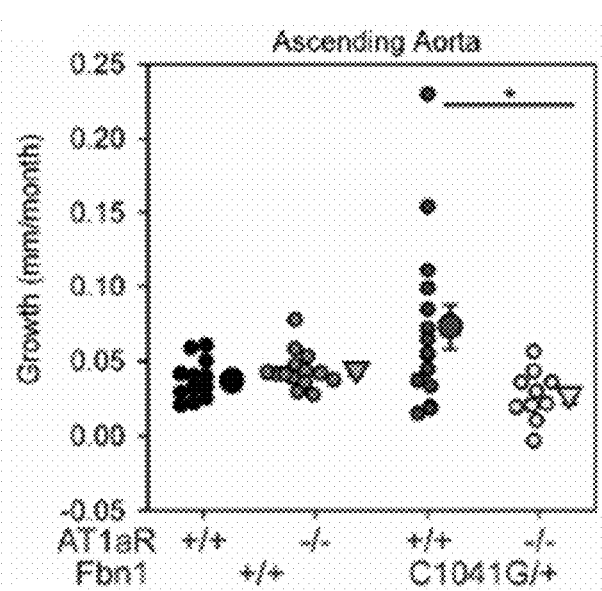
Figure 4C:
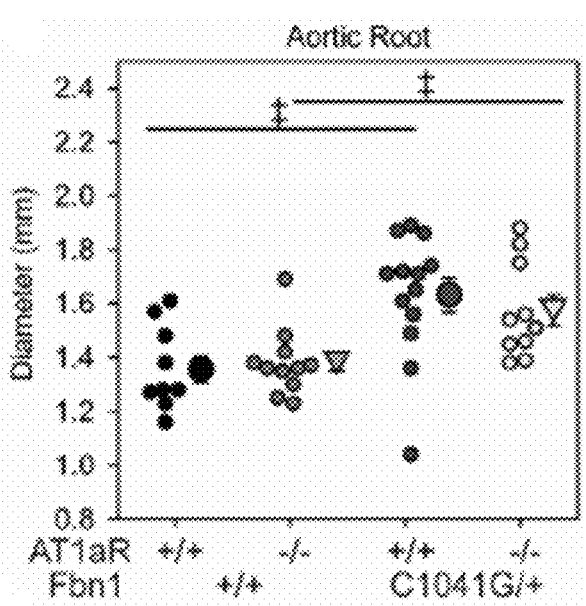
Figure 4D:
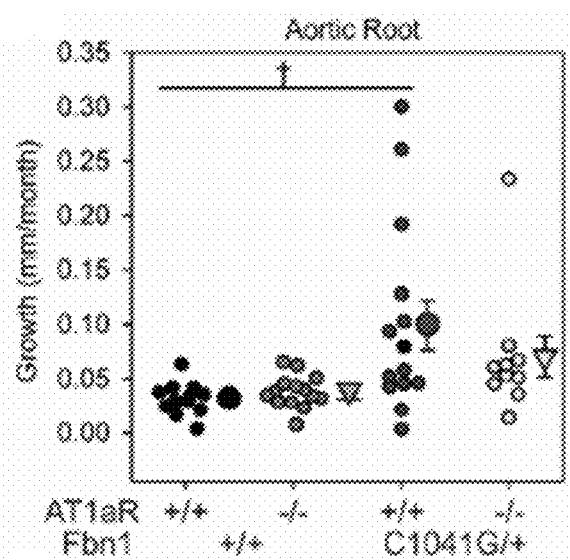

Male $Fbn1^{+/+}$ mice had modest increases in diameters of the ascending aorta (FIG. 3B), aortic root (FIG. 3C), and lengths of the ascending aorta (FIG. 3D) during the course of the 12-month study. These increases were not significantly different from increases seen in $Fbn1^{+/+}$ mice that were also AT1aR$^{-/-}$. These findings based on the ultrasound measurements were confirmed at the 12-month interval by direct measurements on in situ aortas (FIGS. 3E and 3F).

Figure 6A:
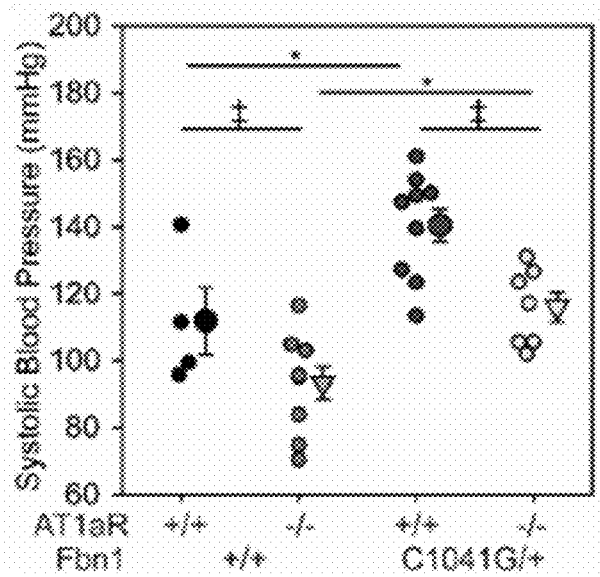
FIGS. 6A-6C. Confounding factors did not contribute to TAA phenotype in male Fbn1C1041G/+ mice.
Figure 6B:
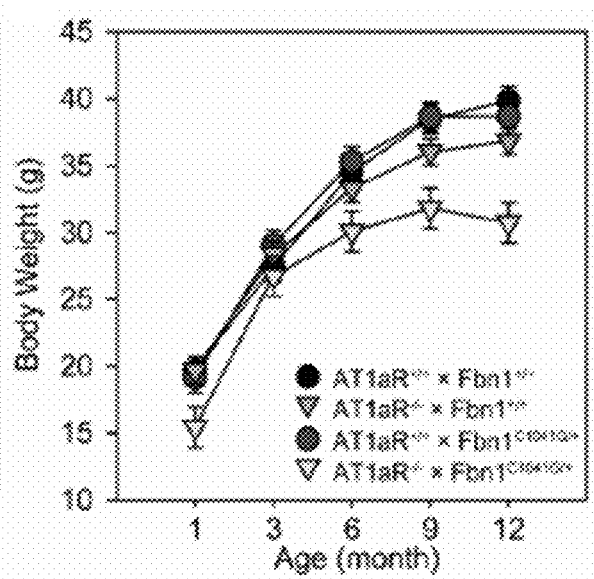
Figure 6C:
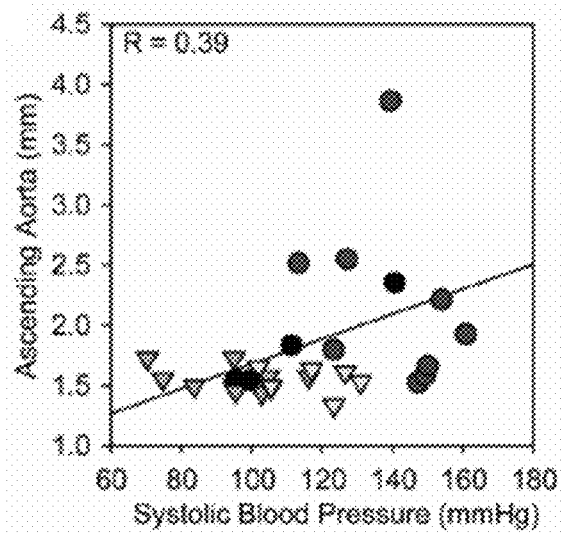

At 1 month of age, male $Fbn1^{C1041G/+}$ mice had increased diameters of ascending aorta and aortic root and lengths of ascending aorta compared to $Fbn1^{+/+}$ mice. At this early age, deletion of AT1aR had no effect on aortic dimensions (FIG. 4). In $Fbn1^{C1041G/+}$ mice that were AT1aR$^{+/+}$, there was a progressive increase in all 3 aorta dimensions acquired by ultrasound. In contrast, deletion of AT1aR markedly attenuated the progressive expansion of these dimensions to rates that were not statistically different from those in $Fbn1^{+/+}$ mice (FIG. 5). As with $Fbn1^{+/+}$ mice, direct aortic measurements in situ at 12 months of age confirmed the data acquired by ultrasound. Consistent with previously published research,(22) body weight and systolic blood pressure were not correlated with ascending aortic dimensions in mice (FIG. 6).

Figure 7A:
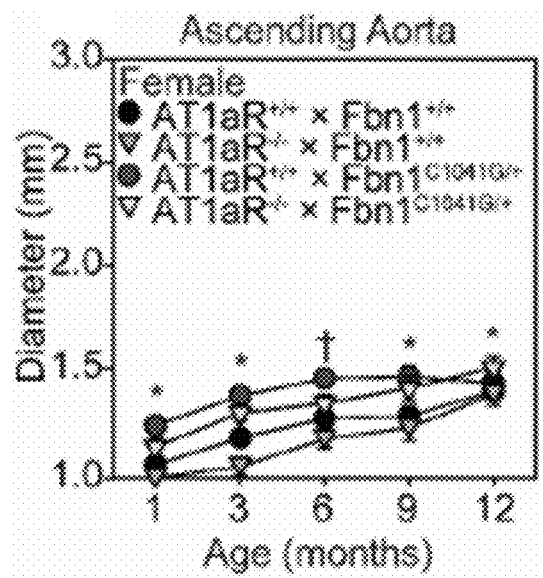
FIGS. 7A-7C. AT1aR deletion had no effect on aortic measurements in female Fbn1C1041G/+ mice. Presented are sequential ultrasound measurements of the; ascending aorta (FIG. 7A), B) aortic root (FIG. 7B), and aortic length (FIG. 7C) in diastole from 1 month to 12 months of age of female $AT1aR^{+/+} \times Fbn1^{+/+}$, $AT1aR^{-/-} \times Fbn1^{+/+}$, $AT1aR^{+/+} \times Fbn1C1041G/+$, and $AT1aR^{-/-} \times Fbn1C1041G/+$ mice. * $p<0.05$ of $AT1aR^{+/+} \times Fbn1^{+/+}$ versus $AT1aR^{+/+} \times Fbn1C1041G/+$; † $p<0.05$ of $AT1aR^{+/+} \times Fbn1C1041G/+$ versus $AT1aR^{-/-} \times Fbn1C1041G/+$; n=7-11/group.
Figure 7B:
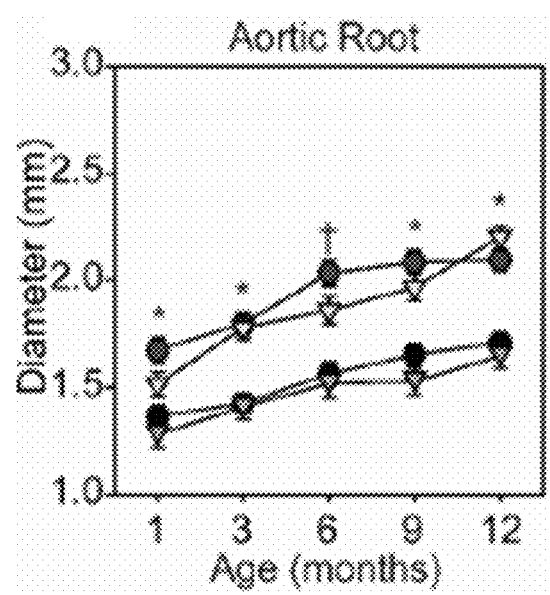
Figure 7C:
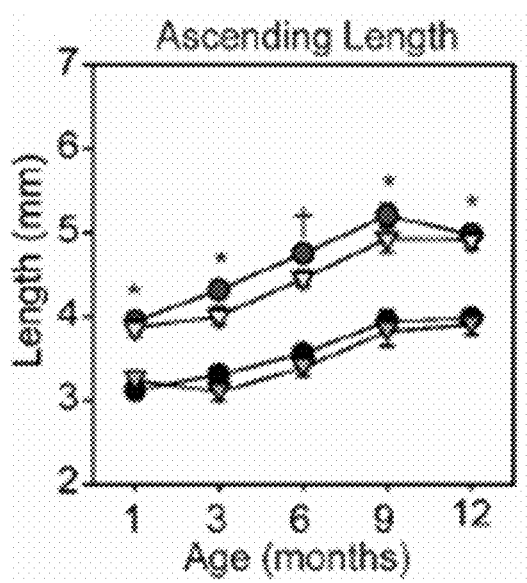
Figure 8A:
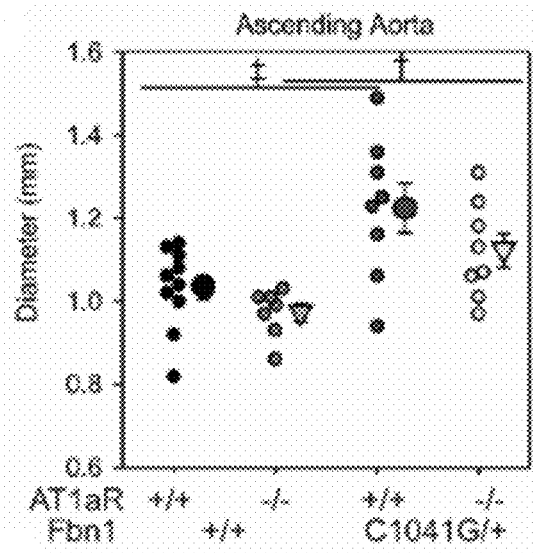
FIGS. 8A-8F. Aortic dimensions at 1 month of age and aortic growth in female mice. Presented are ultrasound measurements of the ascending aorta (FIG. 8A), aortic root (FIG. 8C), and aortic length (FIG. 8E) in diastole at 1 month of age from female $AT1aR^{+/+} \times Fbn1^{+/+}$, $AT1aR^{-/-} \times Fbn1^{+/+}$, $AT1aR^{+/+} \times Fbn1C1041G/+$, and $AT1aR^{-/-} \times Fbn1C1041G/+$ mice. Mean monthly growth is presented, including ascending aorta growth (FIG. 8B), aortic root growth (FIG. 8D), and aortic length growth (FIG. 8F) from 1 month to 12 months in female AT1aR$^{+/+}$×Fbn1$^{+/+}$, AT1aR$^{-/-}$×Fbn1$^{+/+}$, AT1aR$^{+/+}$×Fbn1C1041G/+, and AT1aR$^{-/-}$×Fbn1C1041G/+ mice. * $p<0.05$, † $p<0.01$, ‡ $p<0.001$; n=7-11/group.
Figure 8B:
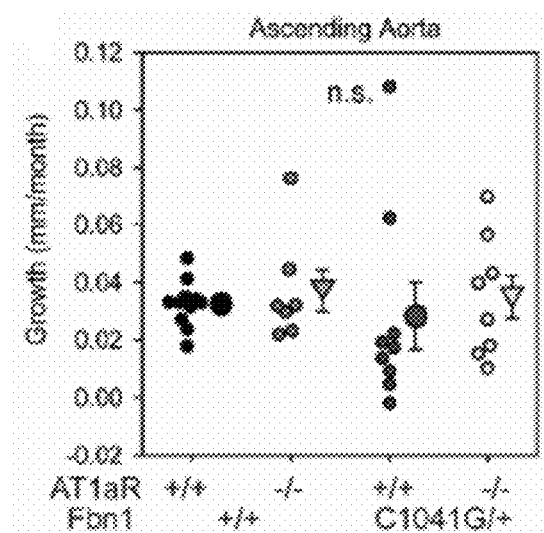
Figure 8C:
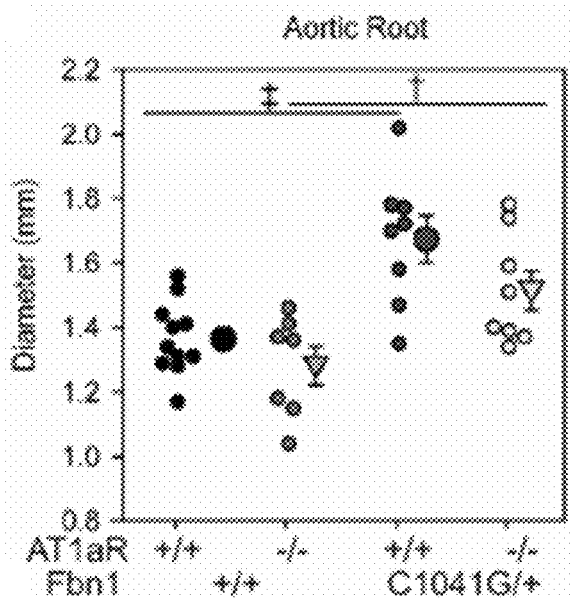
Figure 8D:
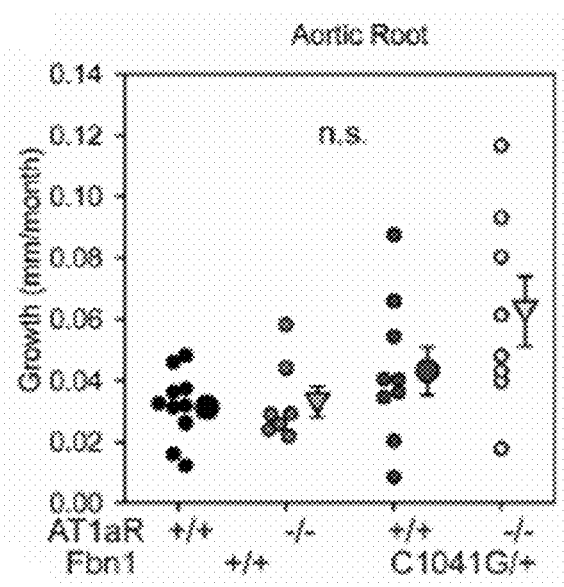
Figure 8E:
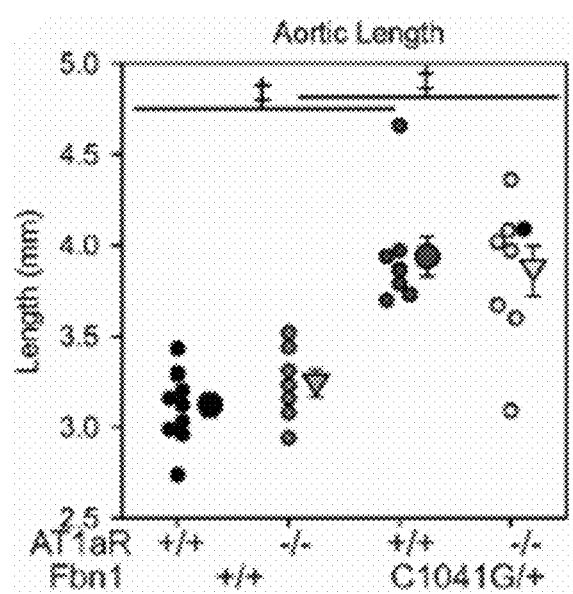
Figure 8F:
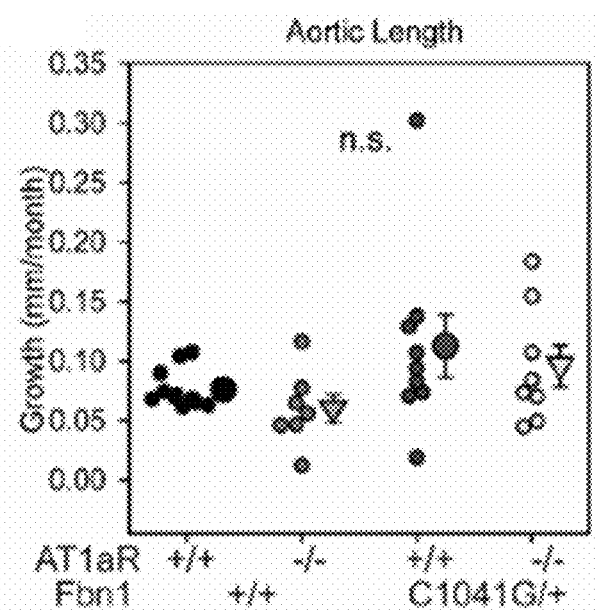
Figures 9A, 9B, 9C:
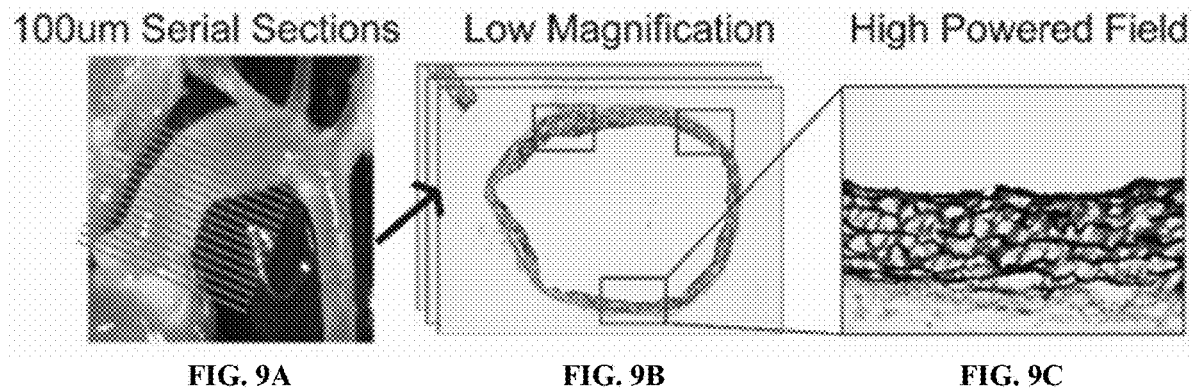
FIGS. 9A-9G. Generation of ascending aortic sections to measure elastin fragmentation and medial thickening. Serial sections (lines in FIG. 9A) of ascending aortas were generated and used for histology. Three high powered fields/section (boxes in FIG. 9B, with high powered magnification in FIG. 9C) were imaged and quantified per biological replicate. Quantification of elastin fragmentation (FIG. 9D, triangle) and medial thickening (FIG. 9D, inverted double arrow) by two independent observers demonstrated good agreement in both measures via Bland-Altman analysis (FIG. 9E).
Figure 9D:
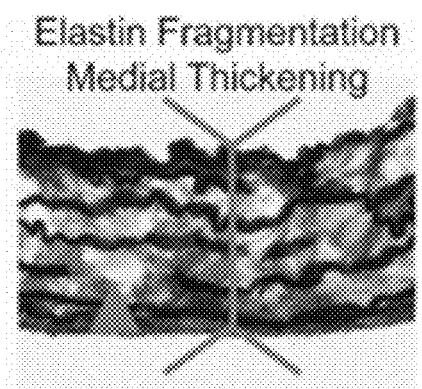
Figure 9E:
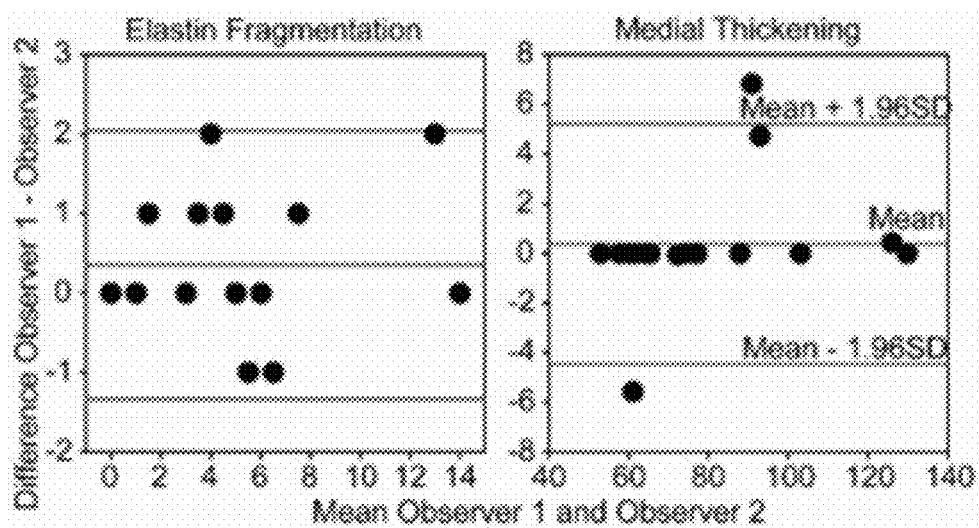
Figure 9F:
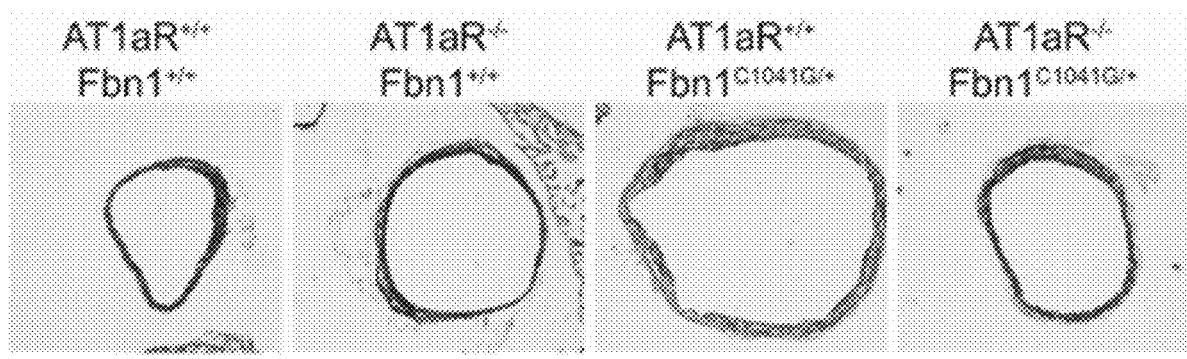
Figure 9G:
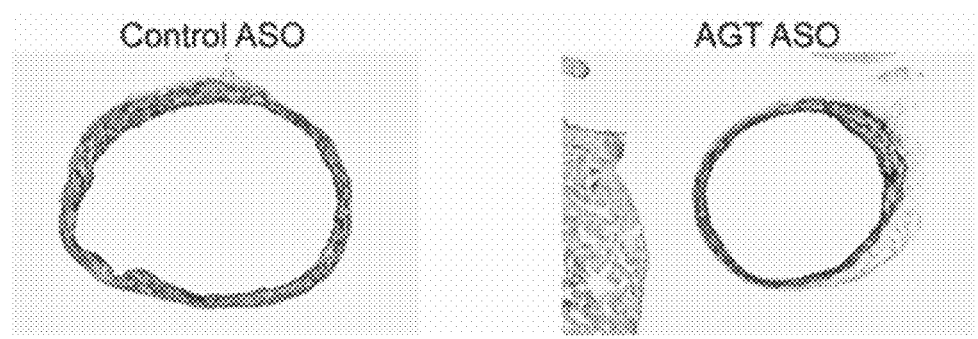

Female $Fbn1^{+/+}$ and $Fbn1^{C1041G/+}$ mice that were with either AT1aR$^{+/+}$ or $^{-/-}$ were also generated and aortic dimensions measured up to 12 months of age. As noted above, beyond the initial differences at 1 month of age, progressive changes in aortic dimensions were not different between $Fbn1^{+/+}$ and $Fbn1^{C1041G/+}$ female mice. The deletion of AT1aR had no effect on the age-related changes in either group (FIGS. 7 and 8).

Figure 10A:
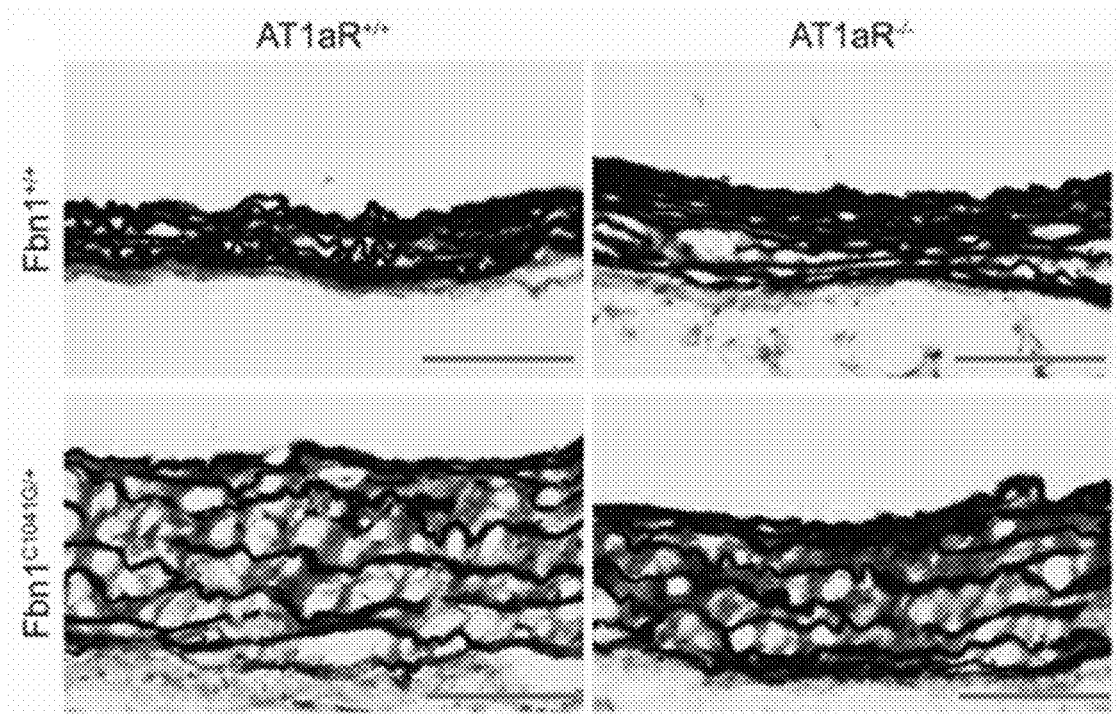
FIGS. 10A-10C. AT1aR deletion attenuated medial remodeling in male Fbn1C1041G/+ mice.
Figure 10B:
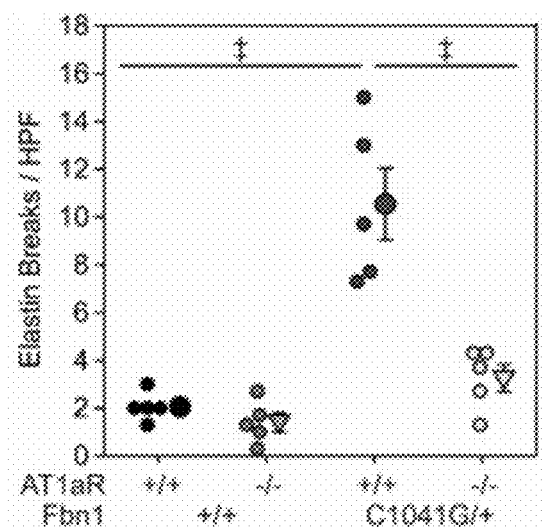
Figure 10C:
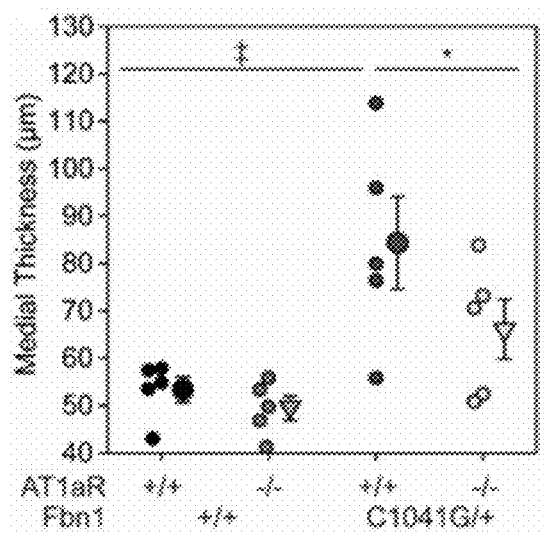

To determine if AT1aR deletion impacted the structure of the aortic media, histological characteristics were determined in aortic tissues acquired at 12 months of age. Since the most dramatic differences in changes of dimensions described above were in the ascending aorta, this region was selected for tissue characterization using the validated and reproducible method (FIG. 9). Ascending aortic tissues from $Fbn1^{+/+}$ mice had elastic fibers with minimal fragmentation (FIG. 10A). Neither the extent of fragmentation nor medial thickness were altered by the absence of AT1aR in $Fbn1^{+/+}$ mice (FIGS. 10B and 10C). In contrast, $Fbn1^{C1041G/+}$×AT1aR$^{+/+}$ mice had extensive fragmentation of elastic fibers and marked medial thickening. Deletion of AT1aR in these mice significantly reduced elastin fragmentation and medial thickening.

Figure 11A:
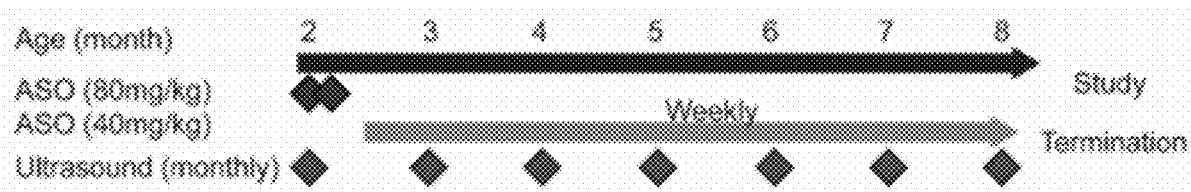
FIGS. 11A-11G. AGT ASOs depleted AGT and attenuated TAA in male Fbn1C1041G/+ mice.
Figure 11B:
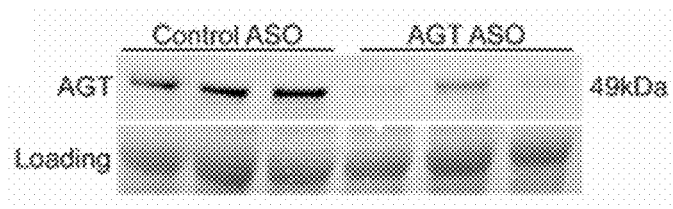

Example 11: Depletion of Plasma AGT Concentrations by AGT ASO Attenuated Aortic Pathology in Male $Fbn1^{C1041G/+}$ Mice It has been demonstrated that administration of AGT ASO markedly reduces plasma concentration of AGT and attenuates AngII responses in mice.(23, 24) Using ASO against the same target as previous publications, male Fbn1$^{C1041G/+}$ mice received a loading dose (80 mg/kg) of either AGT or control ASO on day 1 and day 4 of the study. Starting on day 7, mice received a maintenance dose (40 mg/kg) every 7 days for 6 months. (FIG. 11A). Mice tolerated the ASO well and displayed minimal hepatic and renal toxicity after administration of loading doses (FIG. 12) AGT ASO effectively depleted AGT in plasma (FIG. 11B).

Figure 11C:
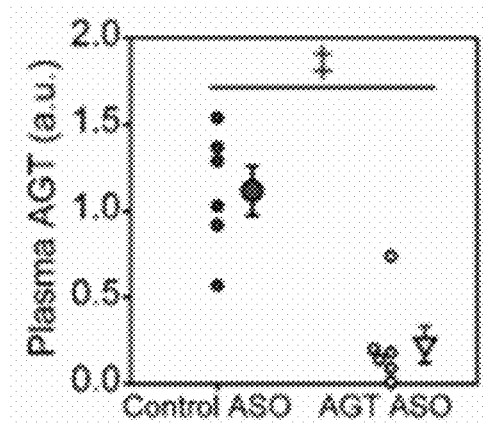
Figure 11D:
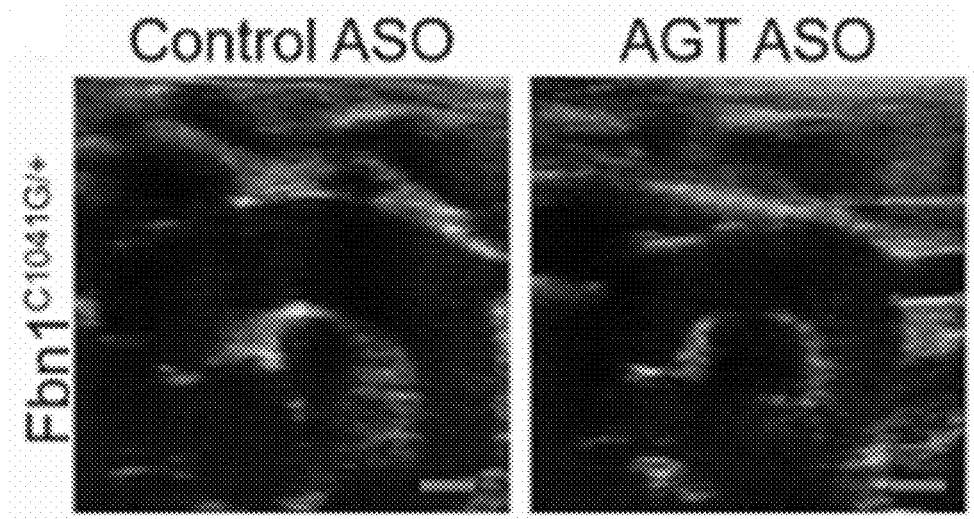
Figure 11E:
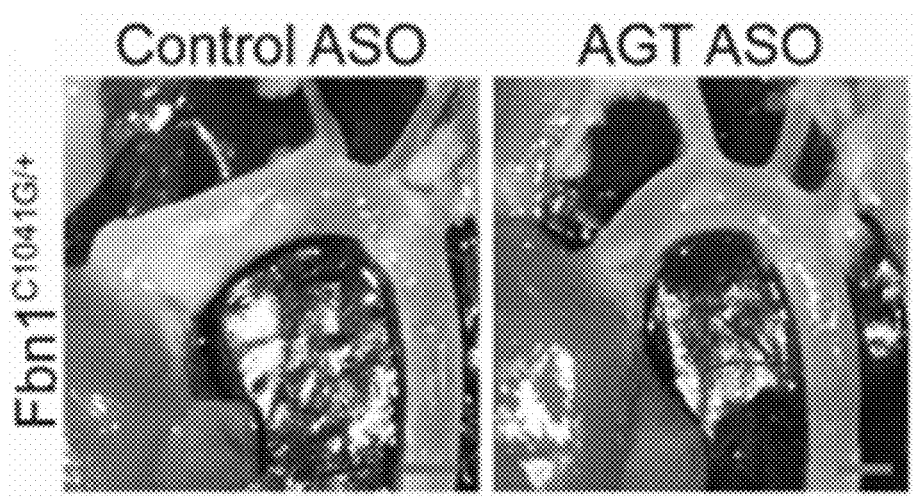
Figure 11F:
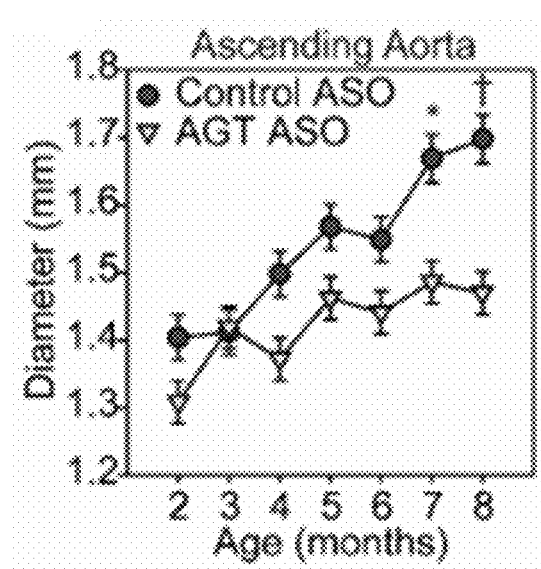
Figure 11G:
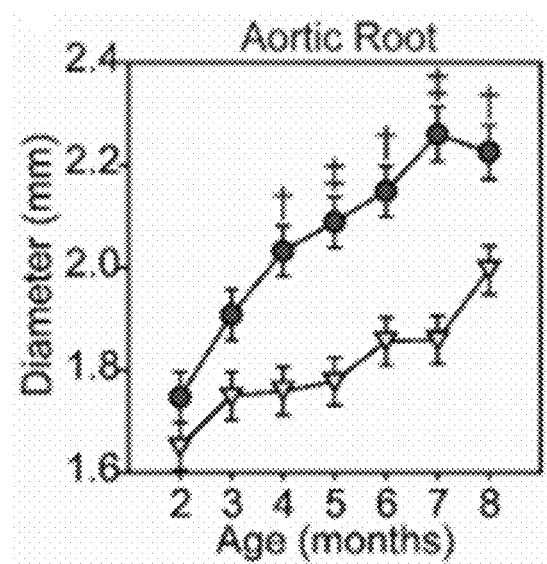
Figure 11H:
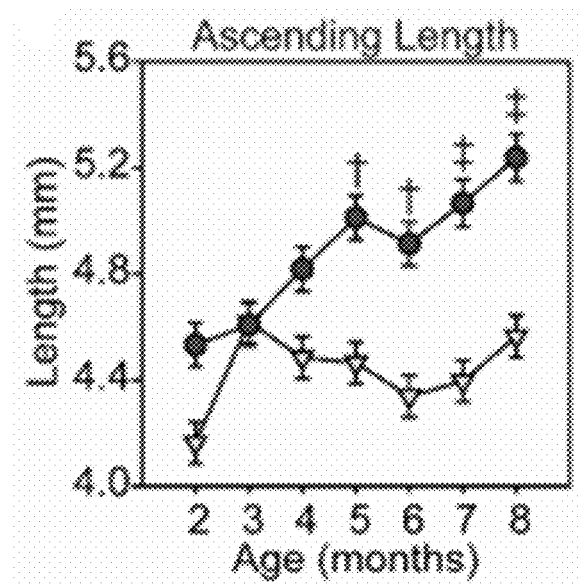
Figure 12A:
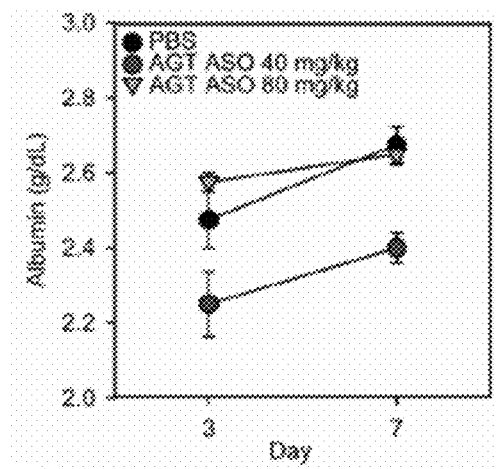
FIGS. 12A-12F. AGT ASOs have low toxicity and effectively reduce circulating AGT. Presented are plasma concentrations of albumin (FIG. 12A), alanine transaminase (AST) (FIG. 12B), aspartate aminotransferase (ALT) (FIG. 12C), total bilirubin (FIG. 12D) blood urea nitrogen (BUN) (FIG. 12E) in mice administered either PBS, AGT ASO (40 mg/kg), or AGT ASO (80 mg/kg) at days 1 and 4. Plasma was taken at days 3 and 7. n=4/group. F) Plasma AGT concentrations at days 3 and 7 detected by Western blotting after AGT ASO was administered at days 1 and 4.
Figure 12B:
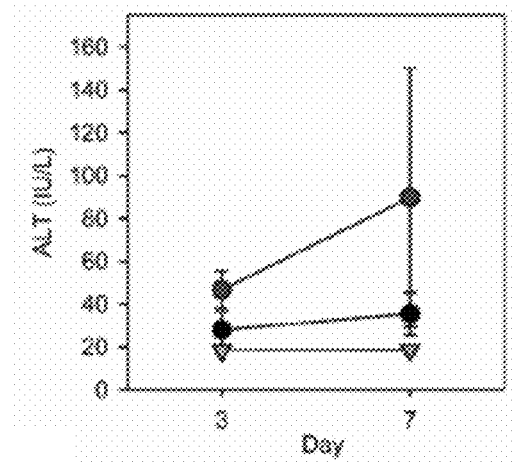
Figure 12C:
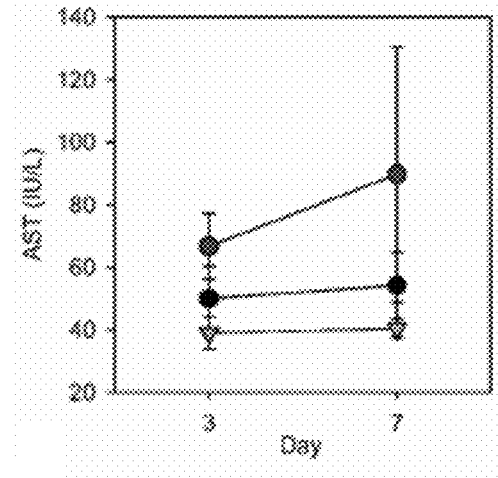
Figure 12D:
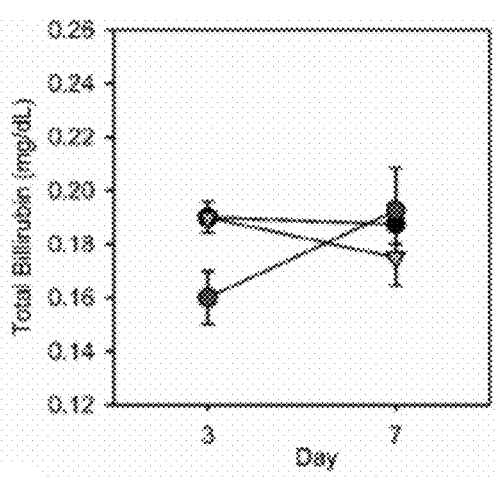
Figure 12E:
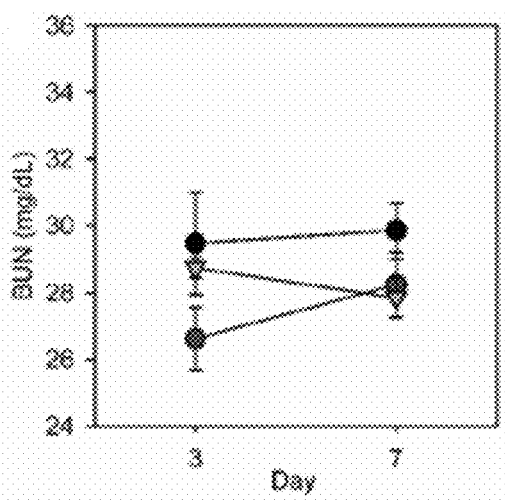
Figure 12F:
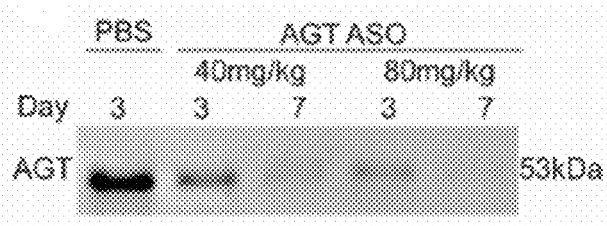

Aortic dimensions were acquired starting at 2 months of age, and every month for a further 6 months using the same process described above (FIG. 11C) with in situ aortic measurements at termination confirming the ultrasound measurement. (FIG. 11D). AGT depletion achieved by the ASO administration led to statistically significant reductions in expansion of diameters of ascending aorta (FIG. 11E) and aortic root (FIG. 11F) and length of ascending aorta (FIG. 11G) in male Fbn1$^{C1041G/+}$ mice.

Figure 13A:
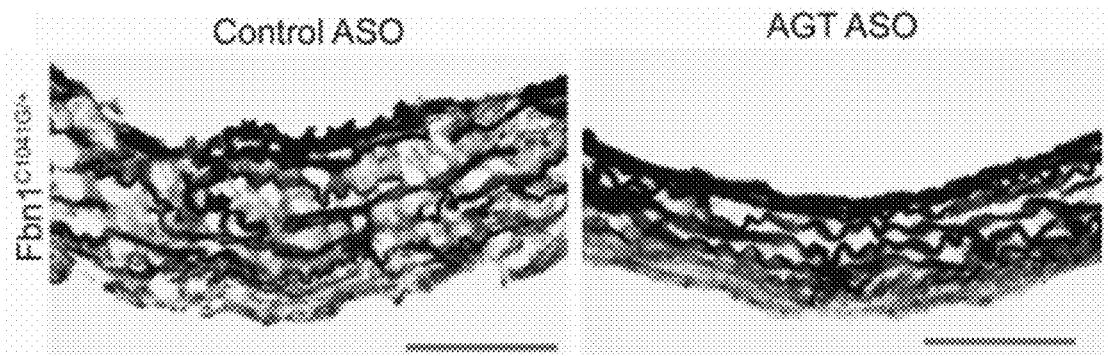
FIGS. 13A-C. AGT ASOs attenuated medial remodeling in male Fbn1$^{C1041G/+}$ mice.
Figure 13B:
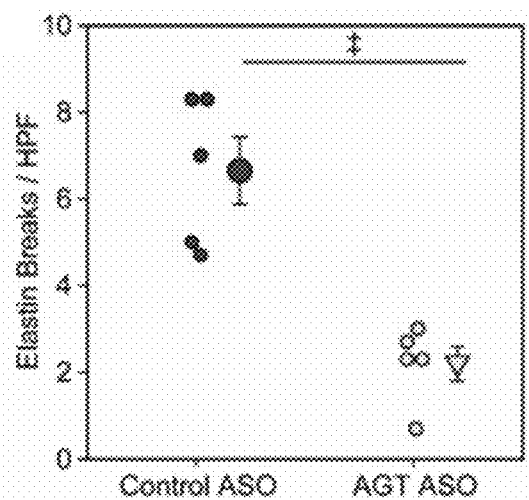
Figure 13C:
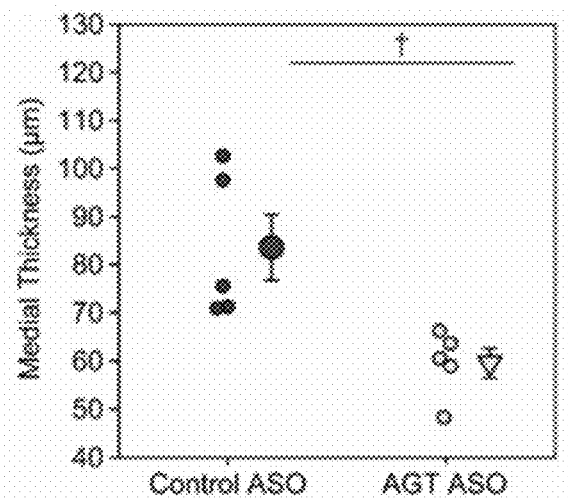
Figure 14:
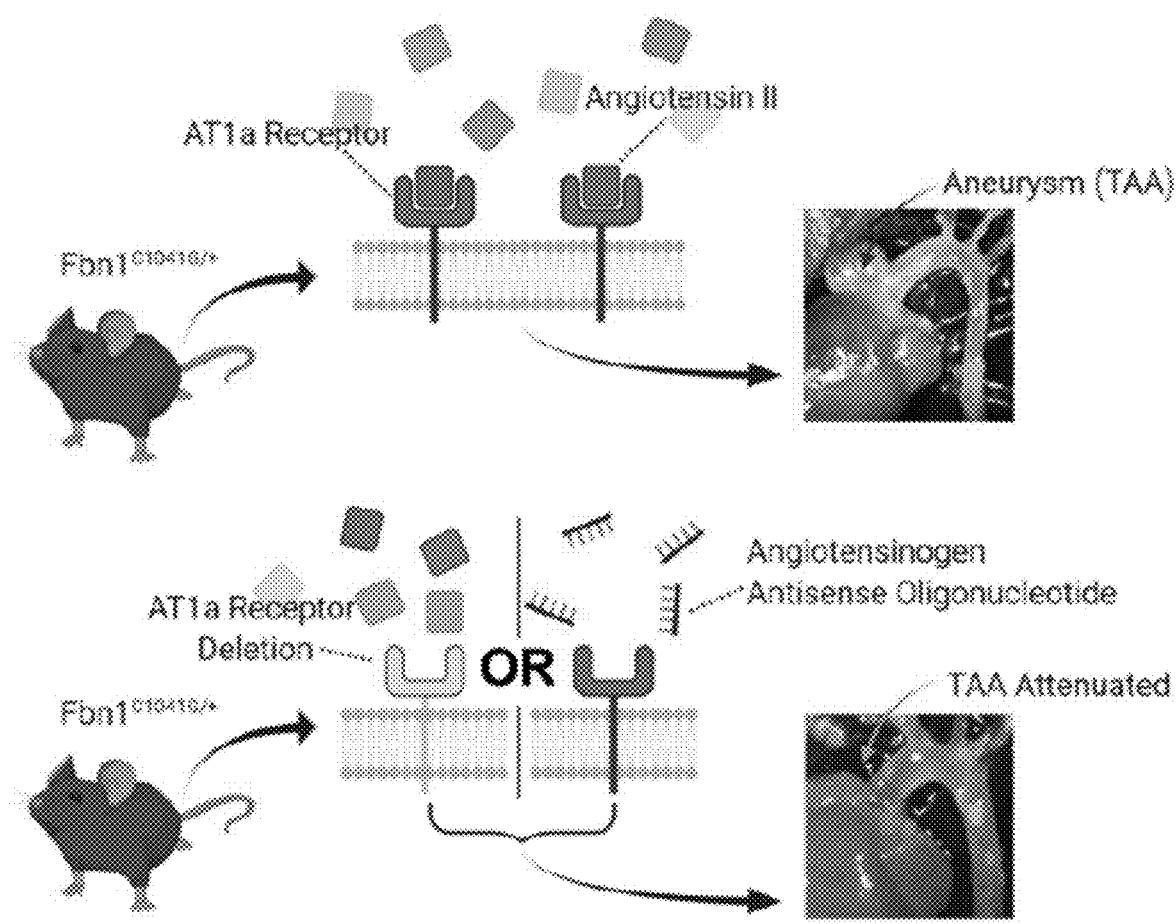
FIG. 14 is a schematic illustration of exemplary results of the studies disclosed herein, which make use of a mouse model of Marfan developed to mimic the human disease. As illustrated, when the AT1a Receptor is deleted or when AGT ASOs are administered, attenuation of TAA is observed.

To determine whether AGT ASO impacted aortic medial structure, histology was performed on ascending aortic tissue. Consistent with previous observation, aortic medial remodeling was detected in 8-month-old male Fbn1$^{C1041G/+}$ mice administered control ASO (FIG. 13A). Compared to male Fbn1$^{C1041G/+}$ mice administered control ASO, male Fbn1$^{C1041G/+}$ mice administered AGT ASO exhibited less elastin fragmentation and medial thickening (FIGS. 13B and 13C).

Discussion of Examples 1-11.

Using pharmacological tools to manipulate the renin angiotensin system, there have been consistent demonstrations that losartan attenuates aortic pathology in mice with fibrillin-1 manipulations.(5, 6, 8, 9, 25, 26, 27) However, it has been proposed that losartan may exert these beneficial actions independent of AT1 receptor antagonism.(6, 8, 9) Additionally, it has been suggested that AngII may not be responsible for cardiovascular pathology in mice with genetically manipulated fibrillin-1.(16) However, the present study demonstrates that both genetic deletion of AT1aR and techniques to reduce AngII availability led to reduced aortic pathology in Fbn1$^{C1041G/+}$ mice. These findings are consistent with ligand activation of AT1aR being the basis for aortic expansion in fibrillin-1 haploinsufficient mice.

The sequential measurement of aortic dimensions over a protracted interval in multiple groups required development of a standardized ultrasound protocol for image acquisition. There is a variance imparted by the differences acquiring dimension at systole or diastole.(20) Given that this excursion can be as much as 0.2 mm, lack of consistency in acquiring data could have a profound effect on data interpretation. The approach used in this study also consistently imaged the aorta from the right parasternal view.(19) While this view is optimal for determining dimensions of the ascending aorta, it is acknowledged that this reduces accuracy of aortic root measurements. In the present study, there was strenuous adherence to a standardized protocol. In addition, the measurements acquired from ultrasound images were validated at termination by direct measurement of aorta in situ. This degree of measurement validation allows us to not only produce reliable data but also reduces the variability between sequential measurements.

There was not any known previous study that defined the effects of sex on the aortic pathology in Fbn1$^{C1041G/+}$ mice. Thus, the initial studies used both males and females. The present study demonstrates a striking effect of sex on the aorta in these mice, with the female Fbn1$^{C1041G/+}$ mice exhibiting minimal progression of thoracic aortic expansion compared to sex-matched Fbn1$^{+/+}$ littermates. In mice with genetic manipulations of Fbn1, there had been only one study indicating that sexual dimorphism existed in the Fbn1GT8/+ mouse model of Marfan syndrome. (28) However, sexual dimorphism of the Fbn1GT8/+ mouse was only defined in the context of pregnancy. In addition to revealing that female Fbn1$^{C1041G/+}$ mice resist aortic dilation, the consequences of this sexual dimorphism on the role of AT1aR deletion was outlined. While the mechanism of this sexual dimorphism is beyond the scope of the present study, it illustrates the need for studies to report data on studies in these mice in a sex-specific manner.

Deletion of AT1aR markedly reduced progression of aortic pathology in male Fbn1$^{C1041G/+}$ mice. AT1 receptors in mice have two isoforms, AT1aR and AT1bR, that resulted from chromosomal duplication. While there is strong sequence homology between the two isoforms, they have different tissue distribution and different signaling mechanisms. Absence of AT1bR has modest effects in vivo, although it is responsible for AngII induced contractions of the infrarenal mouse aorta.(29, 30) Absence of AT1bR has no effect on AngII-induced aortopathies.(29) AT1aR deficient mice were initially demonstrated to have lower blood pressure.(31) However, in agreement with the present study, there has also been several publications showing no difference in blood pressure between AT1aR$^{+/+}$ and mice.(32) While the present study was ongoing, the genetic deletion of AT1aR was reported in Fbn1 hypomorphic mice. While global deletion of AT1aR in Fbn1 hypomorphic mice had no significant effect on the survival, there was decreased aortic expansion in mice that survived to 90 days.(33) This emphasizes the need for further study on the divergent roles of the renin angiotensin system in aneurysm versus rupture/dissection. The early acquisition of ultrasound data in this study also illustrated that there are changes in aortic dimension in the early postnatal interval. Despite the dramatic reduction of progression of aortic dimensions in AT1aR$^{-/-}$ mice following this postnatal interval, the absence of AT1aR failed to affect early changes. This is consistent with temporal-dependent mechanisms of the disease as have been demonstrated previously in Fbn1 hypomorphic mice.(33)

Others have noted that AT1aR deficiency had no effect on expansion of the aortic root at 3 and 6 months of age in Fbn1$^{C1041G/+}$ mice, whereas losartan had a divergent effect and was able to decrease aortic root expansion in these mice.(9) The beneficial effects of losartan were attributed to preservation of endothelial function in an AT1aR independent manner through an alternative VEGFR2/eNOS pathway. The basis for the disparity relative to the present study are not clear. Comparisons are hampered by the paucity of data on the protocol for ultrasound acquisition and on the sex of the mice in each group. Other studies suggested that losartan's protective effect may be due to tumor growth factor 0 inhibition or AngII receptor type 2 hyperstimulation.(5, 8) However, the data indicated that blockade of the AT1aR attenuates Marfan syndrome associated TAA. While the pleotropic effects of losartan may contribute to attenuating thoracic aortopathies, the present study is consistent with the postulate that its benefit is due to inhibition of AT1aR activation.

An ASO was used to decrease the synthesis of the unique precursor of all angiotensin peptides to determine whether AT1aR stimulation in aortopathies required AngII as a ligand. This approach is advantageous over the more common mode of reducing AngII production by inhibiting angiotensin-converting enzyme, which regulates other pathways including the kinin-kallikrein system. Additionally, the protracted half-life of ASO leads to persistent inhibition of AGT synthesis and profound reductions in plasma AGT concentrations. Use of this pharmacologic modality also avoids adverse consequences of genetic deletion of the renin angiotensin system components. Previous genetic approaches have included the use of mice with global deficiencies of AGT. However, these mice have several major developmental abnormalities include poor growth and cardiomyopathy.(34) Inhibition of AGT synthesis by an ASO reduces plasma concentrations by approximately 90% in the postnatal phase with no observable toxicity as demonstrated in the present study and other reports.(23, 35) Therefore, the use of ASO to deplete AGT demonstrated the need for the presence of angiotensin ligands to augment aortic pathology in $Fbn1^{C1041G/+}$ mice.

In humans, randomized control trials of angiotensin receptor blockers have yielded mixed results in Marfan syndrome associated TAA, in contrast to the consistent results that have been generated using mouse models of the disease.(5, 6, 8, 9, 25, 26, 27) Most of the mouse and human studies have been performed using losartan, which is characterized by a relatively short half-life and surmountable antagonism. The deficiencies of this drug were likely to have been ameliorated in mouse studies by consistent delivery, via osmotic pumps and diet, leading to a persistent inhibition. AT1 receptor antagonists with enhanced pharmacological profiles, such as irbesartan and candesartan, would be preferable to test the role of AT1 receptor inhibition in humans. Indeed, it has been demonstrated recently that irbesartan significantly attenuated aortic root expansion in individuals with Marfan syndrome.(36) Conversely, ASO affords chronic and persistent inhibition of AGT synthesis to effect long term depletion of angiotensin ligands. These durable effects of ASO enables inhibition of AGT synthesis to be tested as a possible approach to reduce thoracic aortic dilation in Marfan syndrome.

The study provided strong evidence that both AT1aR deletion and AGT depletion resulted in significant attenuation of aortic dilation and lengthening. These data are consistent with AngII signaling through AT1aR being necessary for TAA progression in male $Fbn1^{C1041G/+}$ mice and that profound and persistent depletion of either component is sufficient to attenuate TAA. This study enables future studies to focus on cell types(s) expressing AT1aR that are stimulated to promote the disease. These studies would give great insight into the role of AT1aR on key spatial and temporal events during TAA development but would require generation of cell-specific and lineage traced AT1aR knockouts in a Marfan mouse model. Collectively, these data indicate that renin angiotensin system blockade holds promise in treating Marfan syndrome associated TAA when durable inhibition is achieved. Durable inhibition would encompass use of angiotensin receptor blockers with long half-lives and unsurmountable modes of inhibition as well as ASO based approaches.

Example 12: Losartan Increases Survival of the $Fbn1^{mgR/mgR}$ Mouse Model of Marfan Syndrome in an Age-Dependent Manner Clinical trials investigating angiotensin receptor blockers (ARB), such as losartan, for attenuation of thoracic aortic aneurysm in people with Marfan syndrome have demonstrated variable efficacy. The study described in this Example was conducted to determine whether the age of mice at the time of losartan initiation affected mortality in fibrillin-1 hypomorphic ($Fbn1^{mgR/mgR}$) mice. $Fbn1^{mgR/mgR}$ is a mouse model of Marfan syndrome that develops severe thoracic aortic aneurysms and death due to aortic rupture.

Male (n=40) and female (n=28) $Fbn1^{mgR/mgR}$ mice were randomized to receive losartan in drinking water (0.6 g/L) starting at either postnatal day 24 (P24) or 50 (P50). Data derived from these mice was compared to littermate $Fbn1^{mgR/mgR}$ (20 males, 14 females) and wild type (15 males, 15 females) mice that were given vehicle only. All mice were terminated at 20 weeks of age. Mice that died during the study were necropsied to determine cause of death.

Figure 15A:
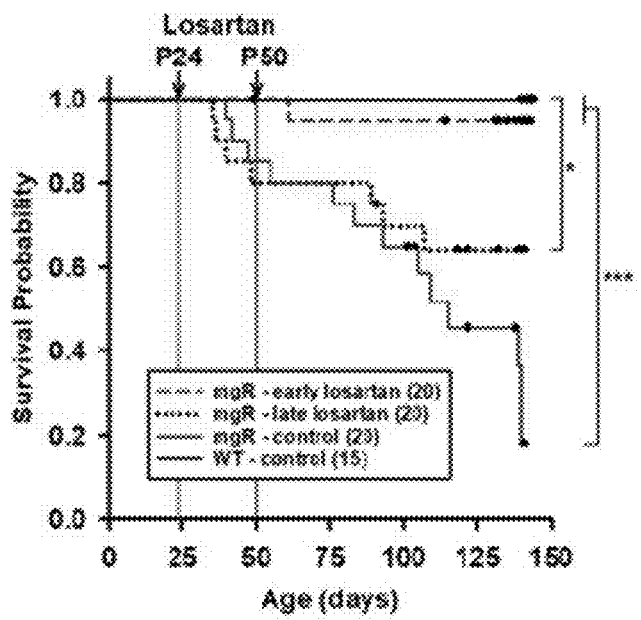
FIGS. 15A and 15B. Losartan increases survival of the Fbn1$^{mgR/mgR}$ mouse model of Marfan syndrome in an age-dependent manner.
Figure 15B:
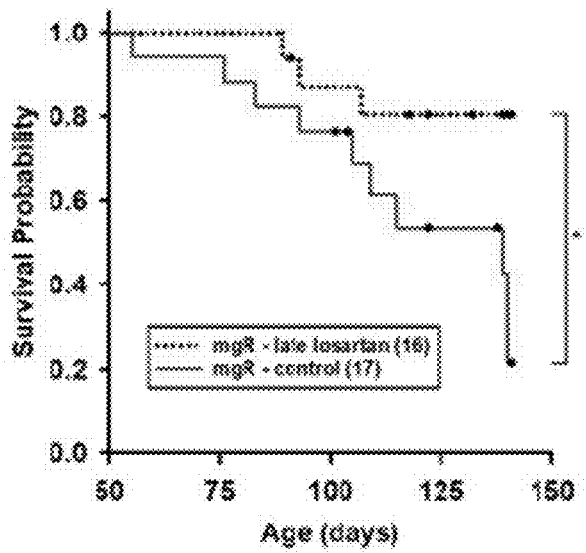

Survival of $Fbn1^{mgR/mgR}$ males receiving losartan at P24 was increased compared to Fbn1mgR/mgR males receiving no drug (p<0.001, log-rank survival) and not different from wild type male mice (p=0.138). Survival of $Fbn1^{mgR/mgR}$ males administered losartan at P50 was not different compared to $Fbn1^{mgR/mgR}$ males receiving no drug (p=0.194) and decreased compared to wild type mice (p=0.002; FIG. 15A). However, several $Fbn1^{mgR/mgR}$ mice died prior to initiation of losartan at P50. To control for these effects, a survival analysis was performed starting at P50, which demonstrated increased survival of $Fbn1^{mgR/mgR}$ males administered losartan at P50 compared to $Fbn1^{mgR/mgR}$ mice receiving no drug (p=0.017; FIG. 15B). Significant differences between groups did not change when survival analysis included deaths due to all-causes.

The findings demonstrate that age is an important variable affecting the therapeutic efficacy of losartan in male $Fbn1^{mgR/mgR}$ mice. Analysis of data reviewed by Milewicz and Ramirez (38) shows that the survival benefit in male $Fbn1^{mgR/mgR}$ mice decreases as age of losartan initiation increases. Human trials have also demonstrated a greater efficacy of therapy at younger ages. Subanalysis of the Pediatric Heart Network trial demonstrated that a younger age of losartan initiation (male less than 16 years old and female less than 15) was associated with a greater decrease in aortic-root z scores over time with both losartan (p=0.002) and atenolol (p<0.001) (37).

One benefit of this study is the ability to detect significant differences in the primary endpoint of survival. The meta-analysis by Al-Abcha et al. (39) found that aortic dilation was attenuated in patients with Marfan syndrome receiving ARB, but no statistically significant difference in the number of clinical events were observed. A median follow-up period of 8 years was necessary for van Andel et al. to demonstrate that losartan administration reduced number the of deaths compared to the control group (0 vs. 5, p=0.14).

The study also demonstrated that survival was significantly lower in male versus female $Fbn1^{mgR/mgR}$ mice (p=0.004), highlighting the impact of sex on disease severity in Marfan syndrome. This sexual dimorphism has been described previously in other Marfan syndrome mouse models and human studies (28). Since survival was not different between $Fbn1^{mgR/mgR}$ and wild type female mice during the length of the study, it was not possible to detect a survival benefit with losartan.

Example 13: Renin-Angiotensin System Inhibitors do not Improve Survival in Fibrillin-1 Hypomorphic Mice with Established Aortic Aneurysm Drugs to attenuate aortic growth are usually not initiated in patients with Marfan syndrome until aortic dilation is already present. This study involved measuring the impact of drugs (the renin-angiotensin system inhibitors losartan and enalapril) on survival and thoracic aortic growth in a mouse model of Marfan syndrome when extensive aortic dilation was already present.

Male and female fibrillin-1 hypomorphic (FBN1 mgR/mgR) mice (n=10-12/group) were stratified into treatment groups by aortic diameter at 6 weeks of age to ensure an equivalent average aortic diameter in each group at the start of the study. Osmotic mini pumps filled with PBS (vehicle), enalapril (2 mg/kg/d), or losartan (20 mg/kg/d) were implanted subcutaneously into mice after stratification. Mini pumps infusing drug or vehicle were replaced every 4 weeks for a total duration of 12 weeks. Wild type littermates (n=10) were infused with PBS as a negative control to the Marfan mouse model. Ascending aortic diameters from male and female FBN1 mgR/mgR mice and their wild type littermates were assessed by ultrasound every 4 weeks from 6 to 18 weeks of age. Aortic diameters were measured luminal edge to luminal edge during diastole.

Six week old $FBN1^{mgR/mgR}$ mice exhibited significantly dilated ascending thoracic aortas at study initiation compared to their wild type sex-matched littermates (in males: $FBN1^{mgR/mgR}$=1.87+/−0.07 mm, wild type=1.23+/−0.07 mm; p<0.001) (in females: $FBN1^{mgR/mgR}$=1.56+/−0.07 mm, wild type=1.18+/−0.07 mm; p<0.001). Baseline mortality of $FBN1^{mgR/mgR}$ mice infused with PBS was 36% in male and 22% in female mice at the time of study termination. Within sex-matched mgR littermates, there was no significant difference in survival between groups treated with PBS, enalapril, or losartan after 12 weeks (p=0.224 for males, p=0.094 in females). In the same groups, no significant difference in maximum ascending aortic diameter was detected after treatment for 12 weeks (in males: PBS=2.69+/−0.19 mm, enalapril=2.04+/−0.27 mm, losartan=2.42+/−0.28 mm; p=0.24) (in females: PBS=1.92+/−0.13, enalapril=1.89+/−0.31, losartan=1.98+/−0.17; p=0.86). Furthermore, aortic diameters in the $FBN1^{mgR/mgR}$ mice were found to demonstrate sexual dimorphism.

This research shows that losartan is not effective when administered after significant thoracic aortic dilation has already occurred in $FBN1^{mgR/mgR}$ mice. This has important translational implications because losartan is usually not started in patients with Marfan syndrome until significant aortic dilation is already present. In addition, this research demonstrates that male $FBN1^{mgR/mgR}$ mice have a significantly larger aortic diameter than female $FBN1^{mgR/mgR}$ mice. This sexual dimorphism has been observed in patients with Marfan syndrome as well.

Figure 16:
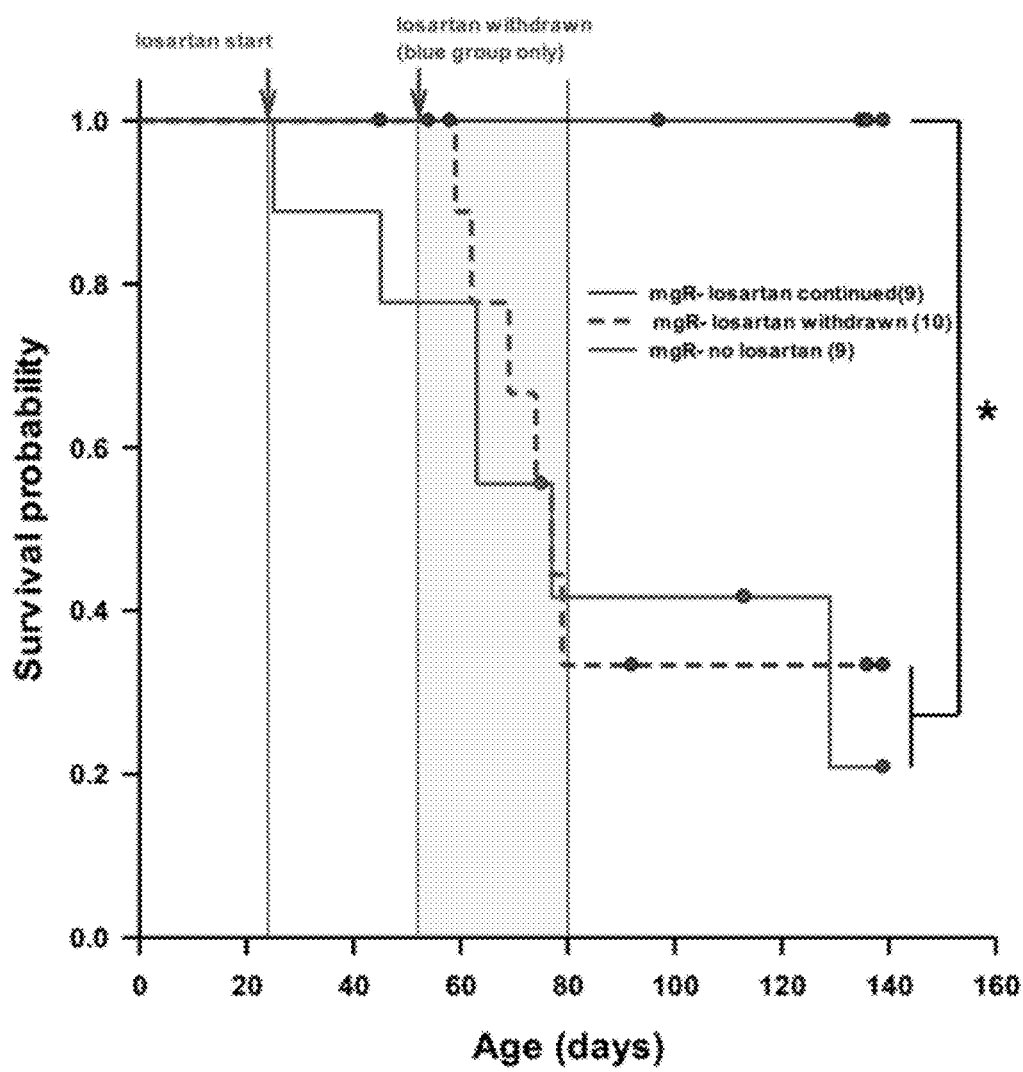
FIG. 16. Increased mortality from thoracic aortic rupture following losartan withdrawal in a mouse model of Marfan Syndrome. Male FBN1$^{mgR/mgR}$ (mgR) mice given losartan in drinking water starting at 24 days of age (dashed line and dark grey line) are protected from mortality due to aortic rupture compared to mgR controls (red line). Withdrawal of losartan during late adolescence (52 days of age) was followed by 6/10 mice dying by aortic rupture within 4 weeks (shaded area). (*=$p<0.05$. Censored data include humane endpoints and non-rupture events.)

Example 14: Increased Death Due to Aortic Rupture in Marfan Syndrome Mouse Model within 30 Days of Losartan Withdrawal With reference to FIG. 16, male $FBN1^{mgR/mgR}$ (mgR) mice that were given losartan in drinking water starting at 24 days of age (dashed line and dark grey line) are protected from mortality due to aortic rupture compared to mgR controls (red line). Withdrawal of losartan during late adolescence (52 days of age) was followed by 6/10 mice dying by aortic rupture within 4 weeks (shaded area). (*=p<0.05. Censored data include humane endpoints and non-rupture events.)

These data illustrate that alternative and/or additional therapeutics are needed, including therapeutics having an increased half-life following administration, which exceeds the half-life of angiotensin-receptor blockers such as losartan. For example, an AGT-ASO could be selected that has a beneficial half-life, e.g., a half-life of about one-month in a patient.

Figure 17:
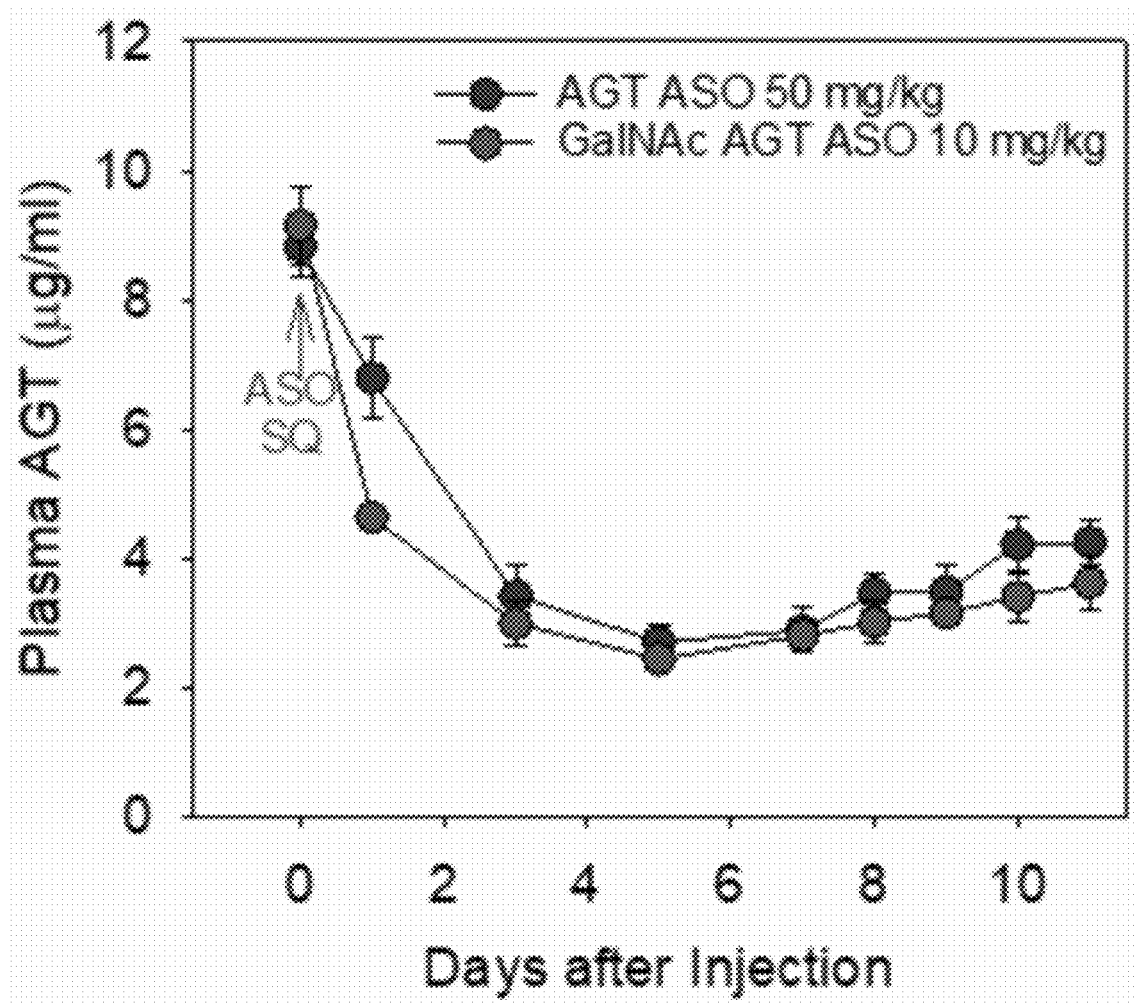
FIG. 17. AGT ASOs result in a sustained reduction in circulating AGT for days after administration. Plasma AGT levels in mice after receiving subcutaneous injection of either AGT ASO (black circle) or GalNAc AGT ASO (dark grey circle) are presented as a function of time.

Example 15: AGT ASOs Result in a Sustained Reduction in Circulating AGT for Days after Administration Male C57BL/6J at 8 weeks of age were injected with either AGT ASO (target AGT globally) or GalNAc AGT ASO (target AGT in liver) subcutaneously (Number=5/group). Day 0 represents prior to ASO injection, and Day 1 represents 1 day after the injection. With reference to FIG. 17, plasma AGT was reduced drastically within 24 hours after the single injection of either AGT ASO or GalNAc AGT ASO, and remained low even after 11 days. Dose of GalNAc AGT ASO was lower but plasma AGT reduction within the first 24 hours was more profound (P<0.01), compared to AGT ASO.

All publications, patents, and patent applications mentioned in this specification are herein incorporated by reference to the same extent as if each individual publication, patent, or patent application was specifically and individually indicated to be incorporated by reference, including the references set forth in the following list:

REFERENCES

1. Lee B, Godfrey M, Vitale E, Hori H, Mattei M G, Sarfarazi M, Tsipouras P, Ramirez F, Hollister D W. Linkage of Marfan Syndrome and a Phenotypically Related Disorder to Two Different Fibrillin Genes. Nature. 1991; 352(6333):330-4. Epub 1991/07/25. doi: 10.1038/352330a0. PubMed PMID: 1852206.
2. Dietz H C, Cutting C R, Pyeritz R E, Maslen C L, Sakai L Y, Corson G M, Puffenberger E G, Hamosh A, Nanthakumar E J, Curristin S M, Stetten G, Meyers D A, Francomano C A. Marfan Syndrome Caused by a Recurrent De Novo Missense Mutation in the Fibrillin Gene. Nature. 1991; 352(6333):337-9. Epub 1991/07/25. doi: 10.1038/352337a0. PubMed PMID: 1852208.
3. Judge D P, Biery N J, Keene D R, Geubtner J, Myers L, Huso D L, Sakai L Y, Dietz H C. Evidence for a Critical Contribution of Haploinsufficiency in the Complex Pathogenesis of Marfan Syndrome. The Journal of clinical investigation. 2004; 114(2):172-81. doi: 10.1172/JCI20641. PubMed PMID: 15254584; PMCID: PMC449744.
4. Brooke B S, Habashi J P, Judge D P, Patel N, Loeys B, Dietz H C, 3rd. Angiotensin Ii Blockade and Aortic-Root Dilation in Marfan's Syndrome. N Engl J Med. 2008; 358(26):2787-95. doi: 10.1056/NEJMoa0706585. PubMed PMID: 18579813; PMCID: PMC2692965.
5. Habashi J P, Judge D P, Holm T M, Cohn R D, Loeys B L, Cooper T K, Myers L, Klein E C, Liu G, Calvi C, Podowski M, Neptune E R, Halushka M K, Bedja D, Gabrielson K, Rifkin D B, Carta L, Ramirez F, Huso D L, Dietz H C. Losartan, an At1 Antagonist, Prevents Aortic Aneurysm in a Mouse Model of Marfan Syndrome. Science. 2006; 312(5770):117-21. doi: 10.1126/science.1124287. PubMed PMID: 16601194; PMCID: PMC1482474.
6. Cook J R, Clayton N P, Carta L, Galatioto J, Chiu E, Smaldone S, Nelson C A, Cheng S H, Wentworth B M, Ramirez F. Dimorphic Effects of Transforming Growth Factor-Beta Signaling During Aortic Aneurysm Progression in Mice Suggest a Combinatorial Therapy for Marfan 7. Gallo E M, Loch D C, Habashi J P, Calderon J F, Chen Y, Bedja D, van Erp C, Gerber E E, Parker S J, Sauls K, Judge D P, Cooke S K, Lindsay M E, Rouf R, Myers L, ap Rhys C M, Kent K C, Norris R A, Huso D L, Dietz H C. Angiotensin Ii-Dependent Tgf-Beta Signaling Contributes to Loeys-Dietz Syndrome Vascular Pathogenesis. The Journal of clinical investigation. 2014; 124(1):448-60. doi: 10.1172/JCI69666. PubMed PMID: 24355923; PMCID: PMC3871227.
8. Habashi J P, Doyle J J, Holm T M, Aziz H, Schoenhoff F, Bedja D, Chen Y, Modiri A N, Judge D P, Dietz H C. Angiotensin Ii Type 2 Receptor Signaling Attenuates Aortic Aneurysm in Mice through Erk Antagonism. Science. 2011; 332(6027):361-5. doi: 10.1126/science.1192152. PubMed PMID: 21493863; PMCID: PMC3097422.
9. Sellers S L, Milad N, Chan R, Mielnik M, Jermilova U, Huang P L, de Crom R, Hirota J A, Hogg J C, Sandor G G, Van Breemen C, Esfandiarei M, Seidman M A, Bernatchez P. Inhibition of Marfan Syndrome Aortic Root Dilation by Losartan: Role of Angiotensin Ii Receptor Type 1-Independent Activation of Endothelial Function. Am J Pathol. 2018; 188(3):574-85. Epub 2018/02/13. doi: 10.1016/j.ajpath.2017.11.006. PubMed PMID: 29433732.
10. Kuang S Q, Geng L, Prakash S K, Cao J M, Guo S, Villamizar C, Kwartler C S, Peters A M, Brasier A R, Milewicz D M. Aortic Remodeling after Transverse Aortic Constriction in Mice Is Attenuated with At1 Receptor Blockade. Arterioscler Thromb Vasc Biol. 2013; 33(9):2172-9. doi: 10.1161/ATVBAHA.113.301624. PubMed PMID: 23868934.
11. Ramnath N W, Hawinkels L J, van Heijningen P M, to Riet L, Paauwe M, Vermeij M, Danser A H, Kanaar R, ten Dijke P, Essers J. Fibulin-4 Deficiency Increases Tgf-Beta Signalling in Aortic Smooth Muscle Cells Due to Elevated Tgf-Beta2 Levels. Sci Rep. 2015; 5:16872. doi: 10.1038/srep16872. PubMed PMID: 26607280; PMCID: PMC4660353.
12. Sadoshima J. Novel at(1) Receptor-Independent Functions of Losartan. Circ Res. 2002; 90(7):754-6. PubMed PMID: 11964366.
13. Yasuda N, Miura S, Akazawa H, Tanaka T, Qin Y, Kiya Y, Imaizumi S, Fujino M, I to K, Zou Y, Fukuhara S, Kunimoto S, Fukuzaki K, Sato T, Ge J, Mochizuki N, Nakaya H, Saku K, Komuro I. Conformational Switch of Angiotensin Ii Type 1 Receptor Underlying Mechanical Stress-Induced Activation. EMBO Rep. 2008; 9(2):179-86. doi: 10.1038/sj.embor.7401157. PubMed PMID: 18202720; PMCID: PMC2246415.
14. Iwasaki H, Yoshimoto T, Sugiyama T, Hirata Y. Activation of Cell Adhesion Kinase Beta by Mechanical Stretch in Vascular Smooth Muscle Cells. Endocrinology. 2003; 144(6):2304-10. Epub 2003/05/15. doi: 10.1210/en.2002-220939. PubMed PMID: 12746290.
15. Schleifenbaum J, Kassmann M, Szijártó I A, Hercule H C, Tano J Y, Weinert S, Heidenreich M, Pathan A R, Anistan Y M, Alenina N, Rusch N J, Bader M, Jentsch T J, Gollasch M. Stretch-Activation of Angiotensin Ii Type 1a Receptors Contributes to the Myogenic Response of Mouse Mesenteric and Renal Arteries. Circ Res. 2014; 115(2):263-72. Epub 2014/05/20. doi: 10.1161/circresaha.115.302882. PubMed PMID: 24838176.
16. Cook J R, Carta L, Benard L, Chemaly E R, Chiu E, Rao S K, Hampton T G, Yurchenco P, Gen TACRC, Costa K D, Hajjar R J, Ramirez F. Abnormal Muscle Mechanosignaling Triggers Cardiomyopathy in Mice with Marfan Syndrome. The Journal of clinical investigation. 2014; 124(3):1329-39. doi: 10.1172/JCI71059. PubMed PMID: 24531548; PMCID: PMC3934180.
17. Robinet P, Milewicz D M, Cassis L A, Leeper N J, Lu H S, Smith J D. Consideration of Sex Differences in Design and Reporting of Experimental Arterial Pathology Studies-Statement from Atvb Council. Arterioscler Thromb Vasc Biol. 2018; 38(2):292-303. Epub 2018/01/06. doi: 10.1161/atvbaha.117.309524. PubMed PMID: 29301789; PMCID: PMC5785439.
18. Daugherty A, Tall A R, Daemen M, Falk E, Fisher E A, Garcia-Cardena G, Lusis A J, Owens A P, 3rd, Rosenfeld M E, Virmani R. Recommendation on Design, Execution, and Reporting of Animal Atherosclerosis Studies: A Scientific Statement from the American Heart Association. Arterioscler Thromb Vasc Biol. 2017; 37(9):e131-e57. Epub 2017/07/22. doi: 10.1161/atv.0000000000000062. PubMed PMID: 28729366.
19. Sawada H, Chen J Z, Wright B C, Moorleghen J J, Lu H S, Daugherty A. Ultrasound Imaging of the Thoracic and Abdominal Aorta in Mice to Determine Aneurysm Dimensions. J Vis Exp. 2019; 8(145):10.3791/59013. Epub 2019/03/26. doi: 10.3791/59013. PubMed PMID: 30907888; PMCID: PMC6594159.
20. Chen J Z, Sawada H, Moorleghen J J, Weiland M, Daugherty A, Sheppard M B. Aortic Strain Correlates with Elastin Fragmentation in Fibrillin-1 Hypomorphic Mice. Circ Rep. 2019; 1(5):199-205. doi: 10.1253/circrep.CR-18-0012. PubMed PMID: 31123721; PMCID: PMC6528667.
21. Sawada H, Chen J Z, Wright B C, Moorleghen J J, Lu H S, Daugherty A. Ultrasound Imaging of the Thoracic and Abdominal Aorta in Mice to Determine Aneurysm Dimensions. J Vis Exp. 2018; 145:e59013. doi: doi: 10.3791/59013.
22. Rateri D L, Davis F M, Balakrishnan A, Howatt D A, Moorleghen J J, O'Connor W N, Charnigo R, Cassis L A, Daugherty A. Angiotensin Ii Induces Region-Specific Medial Disruption During Evolution of Ascending Aortic Aneurysms. Am J Pathol. 2014; 184(9):2586-95. doi: 10.1016/j.ajpath.2014.05.014. PubMed PMID: 25038458; PMCID: PMC25038458.
23. Lu H, Wu C, Howatt D A, Balakrishnan A, Moorleghen J J, Chen X, Zhao M, Graham M J, Mullick A E, Crooke R M, Feldman D L, Cassis L A, Vander Kooi C W, Daugherty A. Angiotensinogen Exerts Effects Independent of Angiotensin Ii. Arterioscler Thromb Vasc Biol. 2016; 36(2):256-65. doi: 10.1161/ATVBAHA.115.306740. PubMed PMID: 26681751; PMCID: PMC4732917.
24. Wu C H, Wang Y, Ma M, Mullick A E, Crooke R M, Graham M J, Daugherty A, Lu H S. Antisense Oligonucleotides Targeting Angiotensinogen: Insights from Animal Studies. Bioscience reports. 2019; 39(1). Epub 2018/12/12. doi: 10.1042/BSR20180201. PubMed PMID: 30530571; PMCID: PMC6328882.
25. Yang H H, Kim J M, Chum E, van Breemen C, Chung A W. Long-Term Effects of Losartan on Structure and Function of the Thoracic Aorta in a Mouse Model of Marfan Syndrome. British journal of pharmacology. 2009; 158(6):1503-12. doi: 10.1111/j.1476-5381.2009.00443.x. PubMed PMID: 19814725; PMCID: PMC2795217.
26. Bhatt A B, Buck J S, Zuflacht J P, Milian J, Kadivar S, Gauvreau K, Singh M N, Creager M A. Distinct Effects of Losartan and Atenolol on Vascular Stiffness in Marfan Syndrome. Vascular medicine (London, England). 2015; 20(4):317-25. Epub 2015/03/22. doi: 10.1177/1358863x15569868. PubMed PMID: 25795452.

27. Hibender S, Franken R, van Roomen C, Ter Braake A, van der Made I, Schermer E E, Gunst Q, van den Hoff M J, Lutgens E, Pinto Y M, Groenink M, Zwinderman A H, Mulder B J, de Vries C J, de Waard V. Resveratrol Inhibits Aortic Root Dilatation in the Fbn1c1039g/+ Marfan Mouse Model. Arterioscler Thromb Vasc Biol. 2016; 36(8):1618-26. doi: 10.1161/ATVBAHA.116.307841. PubMed PMID: 27283746.

28. Renard M, Muino-Mosquera L, Manalo E C, Tufa S, Carlson E J, Keene D R, De Backer J, Sakai L Y. Sex, Pregnancy and Aortic Disease in Marfan Syndrome. PloS one. 2017; 12(7):e0181166. Epub 2017/07/15. doi: 10.1371/journal.pone.0181166. PubMed PMID: 28708846.

29. Poduri A, Owens A P, 3rd, Howatt D A, Moorleghen J J, Balakrishnan A, Cassis L A, Daugherty A. Regional Variation in Aortic At1b Receptor Mrna Abundance Is Associated with Contractility but Unrelated to Atherosclerosis and Aortic Aneurysms. PloS one. 2012; 7(10): e48462. Epub 2012/11/03. doi: 10.1371/journal.pone.0048462. PubMed PMID: 23119030; PMCID: PMC3485205.

30. Zhou Y, Dirksen W P, Babu G J, Periasamy M. Differential Vasoconstrictions Induced by Angiotensin Ii: Role of At1 and At2 Receptors in Isolated C57bl/6j Mouse Blood Vessels. Am J Physiol Heart Circ Physiol. 2003; 285(6):H2797-803. Epub 2003/08/09. doi: 10.1152/ajpheart.00466.2003. PubMed PMID: 12907424.

31. Ito M, Oliverio M I, Mannon P J, Best C F, Maeda N, Smithies O, Coffman T M. Regulation of Blood Pressure by the Type 1a Angiotensin Ii Receptor Gene. Proc Natl Acad Sci USA. 1995; 92(8):3521-5. PubMed PMID: 7724593; PMCID: PMC42199.

32. Mangrum A J, Gomez R A, Norwood V F. Effects of at (1a) Receptor Deletion on Blood Pressure and Sodium Excretion During Altered Dietary Salt Intake. American journal of physiology Renal physiology. 2002; 283(3): F447-53. Epub 2002/08/09. doi: 10.1152/ajprenal.00259.2001. PubMed PMID: 12167595.

33. Galatioto J, Caescu C I, Hansen J, Cook J R, Miramontes I, Iyengar R, Ramirez F. Cell Type-Specific Contributions of the Angiotensin Ii Type 1a Receptor to Aorta Homeostasis and Aneurysmal Disease-Brief Report. Arterioscler Thromb Vasc Biol. 2018; 38(3):588-91. Epub 2018/01/27. doi: 10.1161/ATVBAHA.117.310609. PubMed PMID: 29371244; PMCID: PMC5823778.

34. Ding Y, Stec D E, Sigmund C D. Genetic Evidence That Lethality in Angiotensinogen-Deficient Mice Is Due to Loss of Systemic but Not Renal Angiotensinogen. J Biol Chem. 2001; 276(10):7431-6. Epub 2000/11/30. doi: 10.1074/jbc.M003892200. PubMed PMID: 11096065.

35. Ye F, Wang Y, Wu C, Howatt D A, Wu C H, Balakrishnan A, Mullick A E, Graham M J, Danser A H J, Wang J, Daugherty A, Lu H S. Angiotensinogen and Megalin Interactions Contribute to Atherosclerosis-Brief Report. Arterioscler Thromb Vasc Biol. 2019; 39(2):150-5. Epub 2018/12/21. doi: 10.1161/ATVBAHA.118.311817. PubMed PMID: 30567480; PMCID: PMC6344256.

36. Mullen M, Jin X Y, Child A, Stuart A G, Dodd M, Aragon-Martin J A, Gaze D, Kiotsekoglou A, Yuan L, Hu J, Foley C, Van Dyck L, Knight R, Clayton T, Swan L, Thomson JDR, Erdem G, Crossman D, Flather M, Investigators A. Irbesartan in Marfan Syndrome (Aims): A Double-Blind, Placebo-Controlled Randomised Trial. Lancet. 2020; 394(10216):2263-70. Epub 2019/12/15. doi: 10.1016/S0140-6736(19)32518-8. PubMed PMID: 31836196; PMCID: PMC6934233.

37. Lacro R V, Dietz H C, Sleeper L A, et al. Atenolol versus losartan in children and young adults with Marfan's syndrome. N. Engl. J. Med. 2014; 371:2061-2071.

38. Milewicz D M, Ramirez F. Therapies for thoracic aortic aneurysms and acute aortic dissections. Arterioscler Thromb Vasc Biol 2019; 39:126-136.

39. Al-Abcha A, Saleh Y, Mujer M, et al. Meta-analysis examining the usefulness of angiotensin receptor blockers for the prevention of aortic root dilation in patients with the Marfan syndrome. Am J Cardiol 2020; 128:101-106.

40. Chen, J Z (2020) "Involvement of the Renin Angiotensin System in Marfan Syndrome Associated Thoracic Aortic Aneurysms," Theses and Dissertations—Physiology. 47. uknowledge.uky.edu/physiology etds/47

41. Chen, J. Z., et al. (2020), "Inhibition of Angiotensin II Dependent AT1a Receptor Stimulation Attenuates Thoracic Aortic Pathology in Fibrillin-1$^{C1041G/+}$ Mice," bioRxiv preprint, Jun. 2, 2020, doi: doi.org/10.1101/2020.06.01.127670.

42. Sheppard M B, Chen J Z, Rateri D L, Moorleghen J J, Weiland M, and Daugherty A, (2019) Abstract "Renin-Angiotensin System Inhibitors Do Not Improve Survival in Fibrillin-1 Hypomorphic Mice with Established Aortic Aneurysm," J Clin Transl Sci. 2019 March; 3(Suppl 1): 112-113.

43. Smith J D, Chen J Z, Phillips R, Daugherty A, Sheppard M B, (2021) "Losartan Increases Survival of the Fbn1mgR/mgR Mouse Model of Marfan Syndrome in an Age-Dependent Manner," bioRxiv preprint, Feb. 20, 2021, doi: doi.org/10.1101/2021.02.19.429438.

44. U.S. Pat. No. 10,912,792 for "Compounds and Methods for Modulating Angiotensinogen Expression" to Mullick et al., Assigned to Ionis Pharmaceuticals, Inc.

45. U.S. Pat. No. 10,709,728 for "Polynucleotide Agent Targeting Angiotensinogen (AGT) and Methods of Use Thereof" to Hinkle, Assigned to Alnylam Pharmaceuticals, Inc.

46. U.S. Patent Application Publication No. 2015/0297629 for "Modulation of Renin-Angiotensin System (RAS) Related Diseases by Angiotensinogen" to Mullick et al, assigned to Ionis Pharmaceuticals, Inc.

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. A method of attenuating aortic pathology in a subject having Marfan syndrome, comprising:
   (a) selecting the subject having Marfan syndrome; and
   (b) administering to the subject a dose comprising an effective amount of an angiotensinogen (AGT) antisense oligonucleotide (ASO) to reduce AGT plasma levels in the subject.

2. The method of claim 1, wherein the attenuation of aortic pathology includes reducing or inhibiting the progression of aortic dilation.

3. The method of claim 2, wherein the reduction of or inhibition of the progression of aortic dilation is in the thoracic region of the artery.

4. The method of claim 2, wherein the reduction of or inhibition of the progression of aortic dilation is in the aortic root.

5. The method of claim 2, wherein the reduction of or inhibition of the progression of aortic dilation is in the ascending aorta.

6. The method of claim 1, wherein the attenuation of aortic pathology includes reducing the risk of thoracic aortic aneurysm (TAA).

7. The method of claim 1, and further comprising identifying the subject has having an aortic dilation.

8. The method of claim 1, and further comprising identifying the subject as currently receiving treatment with an angiotensin receptor blocker (ARB).

9. The method of claim 8, wherein the ARB is losartan.

10. The method of claim 9, and further comprising initiating administration of the AGT ASO prior to withdrawal of losartan.

11. The method of claim 1, and further comprising concomitantly administering an ARB with the AGT ASO.

12. The method of claim 11, wherein the ARB is losartan.

13. The method of claim 1, and further comprising administration of a subsequent dose of the AGT ASO about 7 days after the previous dose.

14. The method of claim 1, and further comprising administration of a subsequent dose of the AGT ASO about 14 days after the previous dose.

15. The method of claim 1, wherein the administration of the AGT ASO is by parenteral administration.

16. The method of claim 1, wherein the subject is male.

17. The method of claim 1, wherein the subject is younger than 16.

18. The method of claim 1, wherein the subject is human.

19. The method of claim 1, wherein the AGT ASO comprises a sequence selected from the group consisting of SEQ ID NOS: 1 and 2.

20. The method of claim 1, wherein the AGT ASO is modified with N-Acetylgalactosamine (GalNAc).

* * * * *